United States Patent [19]

Morisawa et al.

[11] Patent Number: 4,914,093
[45] Date of Patent: Apr. 3, 1990

[54] PYRIDAZINONE DERIVATIVES, THEIR PREPARATION AND USE

[75] Inventors: Yasuhiro Morisawa; Mitsuru Kataoka; Seiji Kumakura; Hiroyuki Koike; Shinsaku Kobayashi, all of Tokyo, Japan

[73] Assignee: Sankyo Company Limited, Tokyo, Japan

[21] Appl. No.: 325,112

[22] Filed: Mar. 16, 1989

Related U.S. Application Data

[63] Continuation of Ser. No. 102,756, Sep. 24, 1987, abandoned, which is a continuation of Ser. No. 785,452, Oct. 8, 1985, abandoned.

[30] Foreign Application Priority Data

Oct. 12, 1984 [JP] Japan ................................. 59-213968

[51] Int. Cl.$^4$ .................. C07D 237/04; C07D 237/14; C07D 403/12; A61K 31/50
[52] U.S. Cl. .................................... 514/211; 514/247; 514/252; 514/253; 514/227.8; 514/232.2; 514/236.5; 540/575; 544/60; 544/114; 544/121; 544/238; 544/239
[58] Field of Search ................. 544/238, 239, 60, 114; 514/247, 252, 253, 211, 222, 228, 230, 234, 235; 540/575

[56] References Cited

FOREIGN PATENT DOCUMENTS 1383906 2/1975 United Kingdom.
1488330 12/1977 United Kingdom.

OTHER PUBLICATIONS

Zoller, Chem Abs 102, 220886h (1985).
Derwent for Japan 8015/83 (1983).

*Primary Examiner*—Mark L. Berch
*Attorney, Agent, or Firm*—Frishauf, Holtz, Goodman & Woodward

[57] ABSTRACT

Compounds of formula (I):

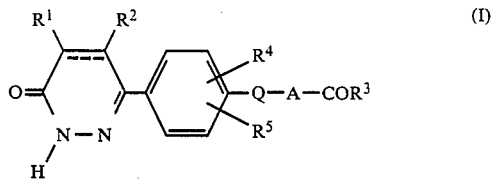

(wherein Q is oxygen or sulfur, the dotted line is a single or double bond, A is alkylene, and $R^1$-$R^5$ are a variety of atoms or organic groups) have excellent ability to potentiate myocardial contractivity and a variety of other properties, and can be used to treat cardiac disorders.

31 Claims, No Drawings

PYRIDAZINONE DERIVATIVES, THEIR PREPARATION AND USE

This application is a continuation of application Ser. No. 102,756, filed Sept. 24, 1987, which is a continuation of Ser. No. 785,452, filed Oct. 8, 1985, both now abandoned.

BACKGROUND OF THE INVENTION

The present invention relates to a series of novel 6-(4-substituted phenyl-3(2H)-pyridazinone derivatives and provides processes for their preparation, methods of using them and compositions containing them. The compounds of the invention are characterized by having a substituent on the 4-position of the phenyl group, which substituent is chosen from a limited class of substituted carbonylalkoxy or carbonylalkylthio groups.

The compounds of the invention have exhibited a variety of valuable therapeutic activities, including myocardial contractivity (notably a stimulant activity arising from potentiation of the contractions of the heart), anti-hypertensive activity, the ability to inhibit gastric secretions and the ability to inhibit platelet aggregation; however, it is envisaged that the primary value of the compounds of the invention will arise as a result of their myocardial contractivity.

A variety of 6-(substituted phenyl)-3(2H)-pyridazinones is known, and some of these are known to have useful cardiac activities. For example, certain such compounds are said in Japanese Patent Applications Kokai (i.e. as laid open to public inspection) No. 18884/72 and No. 8015/83 to have cardiac and anti-hypertensive activities. Other, similar, compounds are disclosed in British Patent Specification No. 1,383,906 (equivalent to U.S. Pat. No. 3,975,388 and U.S. Pat. No. 4,088,762) and these are said to have anti-hypertensive activity. British Patent Specification No. 1,488,330 discloses such compounds for use as β-adrenergic blocking agents. Certain other such compounds are disclosed in J. Het. Chem., 11, 755 (1974), but only in the context of the discussion of synthetic procedures and no utility is disclosed for such compounds.

The prior art compounds referred to above differ from the compounds of the present invention in that the compounds of the invention all contain a substituted carbonylalkoxy or carbonylalkylthio substituent on the 4-position of the phenyl group and we have surprisingly found that certain compounds containing such a substituent possess significantly better myocardial contractivity than do the prior art compounds.

BRIEF SUMMARY OF INVENTION

It is, therefore, an object of the present invention to provide a series of pyridazinone derivatives possessing myocardial contractivity.

It is a further object of the invention to provide a process for preparing such compounds.

It is still a further object of the invention to provide for the use of such compounds to treat a variety of ailments, including cardiac insufficiency.

The compounds of the invention may be represented by the formula (I):

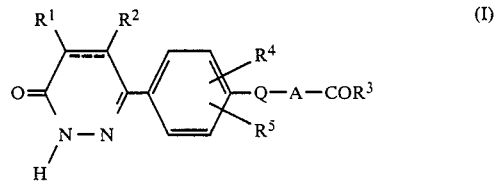

wherein:

$R^1$ and $R^2$ are independently selected from the group consisting of hydrogen atoms and $C_1$-$C_6$ alkyl groups;

Q represents an oxygen atom or a sulfur atom;

A represents a $C_1$-$C_6$ alkylene group;

$R^3$ represents a hydroxy group, a $C_1$-$C_6$ alkoxy group, an aryloxy group, an aralkyloxy group in which the alkyl part has from 1 to 6 carbon atoms, a group of formula $-(NH)_n-NR^6R^7$, wherein n is 0 or 1; and $R^6$ and $R^7$ are independently selected from the group consisting of hydrogen atoms, $C_1$-$C_{10}$ alkyl groups, substituted $C_1$-$C_{10}$ alkyl groups having at least one substituent selected from the group consisting of:

(a) halogen atoms, hydroxy groups, $C_1$-$C_6$ alkoxy groups, aryloxy groups, amino groups, amino groups having one or two substituents selected from the group consisting of $C_1$-$C_6$ alkyl groups, aryl groups and heterocyclic groups, carboxy groups, aliphatic and carbocyclic aromatic acyl groups, substituted $C_2$-$C_8$ aliphatic carboxylic acyl groups having at least one substituent selected from substituents (b) defined hereafter, aliphatic and carbocyclic aromatic carboxylic acylamino groups, $C_2$-$C_7$ alkoxycarbonyl groups, aralkyloxycarbonyl groups where the alkyl part is $C_1$-$C_6$ alkyl, $C_3$-$C_7$ cycloalkyl groups, heterocyclic groups, aryl groups, $C_1$-$C_6$ alkylsulfonyl groups, arylsulfonyl groups, sulfamoyl groups, carbamoyl groups, carbamoyl groups having one or two $C_1$-$C_6$ alkyl substituents, and carbonyl groups having a heterocyclic substituent, $C_2$-$C_6$ alkenyl groups, $C_3$-$C_7$ cycloalkyl groups, aryl groups and heterocyclic groups, or $R^6$ and $R^7$, together with the nitrogen atom to which they are attached, form a heterocyclic group;

a group of formula $-NH-NH-R^8$, wherein:

$R^8$ represents a $C_1$-$C_8$ aliphatic carboxylic acyl group, a $C_2$-$C_8$ substituted aliphatic carboxylic acyl group having at least one substituent selected from the group consisting of:

(b) halogen atoms, $C_1$-$C_6$ alkoxy groups, $C_3$-$C_7$ cycloalkyl groups, aryl groups and heterocyclic groups, a $C_2$-$C_7$ alkoxycarbonyl group, a cinnamoyl group or a carbocyclic aromatic carboxylic acyl group;

or a group of formula $-NH-N=CH-R^9$, wherein:

$R^9$ represents a $C_1$-$C_6$ alkyl group, a $C_1$-$C_6$ alkyl group having at least one halogen substituent or an aryl group;

$R^4$ and $R^5$ are independently selected from the group consisting of hydrogen atoms, $C_1$-$C_6$ alkyl groups, $C_1$-$C_6$ alkyl groups having at least one halogen substituent, halogen atoms, $C_1$-$C_6$ alkoxy groups, $C_1$–$C_7$ aliphatic carboxylic acyloxy groups, amino groups, mono- and di-alkylamino groups where the or each alkyl group is $C_1$–$C_6$ alkyl, $C_1$–$C_7$ aliphatic carboxylic acylamino groups, carboxy groups, $C_2$–$C_7$ alkoxycarbonyl groups, carbamoyl groups, carbamoyl groups having 1 or 2 $C_1$–$C_6$ alkyl substituents, ureido groups, alkylureido groups wherein the alkyl group is $C_1$–$C_6$ alkyl, thioureido groups, alkylthioureido groups wherein the alkyl group is $C_1$–$C_6$ alkyl, cyano groups and nitro groups;

said aryl groups and aryl parts of groups containing an aryl group are $C_6$–$C_{14}$ carbocyclic aryl groups which are unsubstituted or have at least one substituent selected from the group consisting of substituents (a), $C_1$–$C_6$ alkyl groups and $C_1$–$C_6$ alkyl groups having at least one substituent selected from the group consisting of substituents (a);

said heterocyclic groups contain from 5 to 14 ring atoms, of which from 1 to 5 are hetero-atoms selected from the group consisting of nitrogen, oxygen and sulfur atoms, said heterocyclic groups being unsubstituted or having at least one substituent selected from the group consisting of said substituents (a), oxygen atoms, $C_1$–$C_6$ alkyl groups and $C_1$–$C_6$ alkyl groups having at least one substituent selected from the group consisting of said substituents (a); and the dotted line indicates a single or double carbon-carbon bond between the carbon atoms at the 4- and 5-positions of the pyridazinone system;

and pharmaceutically acceptable acid addition salts thereof.

The invention also provides methods of preparing the compounds of the invention, which are described in more detail hereafter.

The invention still further provides a method of treating cardiac disorders in mammals, by administering to said mammal an active compound selected from the group consisting of compounds of formula (I) and pharmaceutically acceptable acid addition salts thereof.

DETAILED DESCRIPTION OF INVENTION

In the compounds of the invention, where $R^1$, $R^2$, $R^4$, $R^5$, $R^9$ or various substituents, as defined above, are $C_1$–$C_6$ alkyl groups, these groups may be straight or branched chain groups and examples include the methyl, ethyl, propyl, isopropyl, butyl, isobutyl, sec-butyl, t-butyl, pentyl, isopentyl, neopentyl, t-pentyl, hexyl and isohexyl groups, of which the $C_1$–$C_4$ alkyl groups, particularly the methyl, ethyl, propyl, isopropyl, butyl, isobutyl and sec-butyl groups, are preferred, the methyl and ethyl groups being more preferred.

Where $R^6$ or $R^7$ represents a $C_1$–$C_{10}$ alkyl group, this likewise may be a straight or branched chain group and examples include the methyl, ethyl, propyl, isopropyl, butyl, isobutyl, sec-butyl, t-butyl, pentyl, isopentyl, neopentyl, t-pentyl, hexyl, isohexyl, heptyl, octyl, nonyl and decyl groups. Where the alkyl group represented by $R^6$ and $R^7$ is unsubstituted, we prefer the groups selected from those defined above which have from 1 to 8 carbon atoms. On the other hand, where the group represented by $R^6$ or $R^7$ is substituted, we prefer that the groups should be chosen from those having from 1 to 6 carbon atoms, more preferably from 2 to 4 carbon atoms.

Where $R^4$, $R^5$ or $R^9$ represents a $C_1$–$C_6$ alkyl group having at least one halogen substituent, the halogen substituent is preferably selected from the group consisting of fluorine, chlorine, bromine and iodine atoms, more preferably fluorine and chlorine atoms. The alkyl group itself may be a straight or branched chain alkyl group and examples of such groups are given above in relation to the groups which may be represented by, inter alia, $R^4$ and $R^5$; the alkyl group is more preferably a $C_1$–$C_4$ alkyl group, for example a methyl, ethyl, propyl, isopropyl or butyl group. The number of halogen substituents is limited only by the number of carbon atoms available to substitute and the substituted alkyl group could be anything from a monohaloalkyl group to a perhaloalkyl group. In general, the most commonly available haloalkyl groups contain 1, 2 or 3 halogen atoms and, for this reason alone, such mono-, di- and tri-haloalkyl groups are preferred, but it should be borne in mind that any greater number of halogen atoms up to complete halogenation is possible. Examples of preferred haloalkyl groups include the fluoromethyl, chloromethyl, trifluoromethyl, 2-chloroethyl, 2,2,2-trichloroethyl and 4-fluorobutyl groups, more preferably the trifluoromethyl group.

Where $R^6$ and/or $R^7$ represents an alkenyl group, this is a straight or branched chain group having from 2 to 6 carbon atoms, more preferably 3 or 4 carbon atoms. Examples of such groups include the vinyl, allyl, 1-propenyl, isopropenyl, methallyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, as well as the branched chain homologs of these groups. Of these, the allyl and methallyl groups are particularly preferred.

Where $R^3$, the substituent (a), the substituent (b), $R^4$ or $R^5$ represents an alkoxy group, this has from 1 to 6 carbon atoms and may be a straight or branched chain alkoxy group. Examples include the methoxy, ethoxy, propoxy, isopropoxy, butoxy, isobutoxy, sec-butoxy, t-butoxy, pentyloxy, isopentyloxy, neopentyloxy, t-pentyloxy, hexyloxy and isohexyloxy groups, of which the $C_1$–$C_4$ alkoxy groups, and particularly the methoxy and ethoxy groups, are more preferred.

Where $R^3$ or the substituent (a) represents an aryloxy group, or substituent (a), the substituent on the substituted amino group of substituent (a), $R^6$, $R^7$, substituent (b) or $R^9$ represents an aryl group, the aryl group is a carbocyclic aryl group having from 6 to 14, preferably from 6 to 10, ring carbon atoms. The aryl group may be a monocyclic or fused polycyclic (preferably bicyclic) group and is more preferably the phenyl, 1-naphthyl or 2-naphthyl group. such groups may be unsubstituted or substituted. Where the group is substituted, the minimum number of substituents is, of course, 1 and the maximum number is dictated by the number of carbon atoms capable of substitution and the nature of the substituents, which may impose steric constraints, as described in more detail hereafter in relation to substituents generally. The nature of the possible substituents is defined more generally above, but, in relation to substituted aryl or aryloxy groups, preferred substituents are $C_1$–$C_6$ (preferably $C_1$–$C_4$) alkyl groups, substituted $C_1$–$C_6$ (preferably $C_1$–$C_4$) alkyl groups (more preferably halogen-substituted alkyl groups), $C_1$–$C_6$ (preferably $C_1$–$C_4$) alkoxy groups, hydroxy groups and halogen atoms. Examples of alkyl, substituted alkyl and alkoxy groups are as given above. Examples of halogen atoms include the fluorine, chlorine, bromine and iodine atoms. Preferred aryl and aryloxy groups are the phenyl and phenoxy groups and, in this case, the most preferred substituents are the methyl, ethyl, trifluoromethyl and methoxy groups and the fluorine and chlorine atoms.

Where $R^3$ represents an aralkyloxy group, the aryl part may be any one of the aryl groups described in the preceding paragraph and the alkyl part is a $C_1$–$C_6$ alkyl group (examples of which are given above), more preferably a $C_1$–$C_3$ alkyl group (e.g. a methyl, ethyl or propyl group) and most preferably a methyl or ethyl group. As with the aryl groups defined above, the aryl part of the aralkyloxy group may be substituted or unsubstituted, and examples of preferred aralkyloxy groups include the benzyloxy, p-methylbenzyloxy p-bromobenzyloxy, m-chlorobenzyloxy, p-methoxybenzyloxy and phenethyloxy groups.

Where the substituent (a), the substituent (b), $R^4$ or $R^5$ represents a halogen atom, this is preferably a fluorine, chlorine, bromine or iodine atom.

Where the substituent (a) is a mono- or di-substituted amino group, the substituent or substituents are chosen from the group consisting of $C_1$–$C_6$ alkyl groups, aryl groups (both of which are as exemplified above) and heterocyclic groups, as defined in more detail below in relation to heterocyclic groups generally.

Where the substituent (a) is an aliphatic or aromatic acylamino group, substituent (a) or $R^8$ is an aliphatic acyl group or a substituted aliphatic acyl group, substituent (a) or $R^8$ is an optionally substituted aromatic acyl group, $R^4$ or $R^5$ is an aliphatic acyloxy group or $R^4$ or $R^5$ is an aliphatic acylamino group, the acyl parts thereof are as described below. Specifically, aliphatic acyl groups are aliphatic carboxylic acyl groups, which may be saturated or unsaturated, having from 1 to 8 carbon atoms [except for the unsubstituted aliphatic acyl groups represented by substituent (a) or $R^8$, which have from 2 to 8 carbon atoms, and the unsaturated aliphatic acyl groups, which necessarily have at least 3 carbon atoms]. Examples of such saturated groups include the formyl, acetyl, propionyl, butyryl, isobutyryl, valeryl, isovaleryl, pivaloyl, hexanoyl, isohexanoyl, heptanoyl and octanoyl groups. The $C_1$–$C_5$ saturated aliphatic acyl groups are preferred (particularly the formyl, acetyl, propionyl, butyryl, valeryl and isovaleryl groups), the acetyl group being the most preferred. In the case of the unsaturated aliphatic acyl groups, these necessarily have a minimum of 3 carbon atoms and so those employed in the present invention have from 3 to 8 carbon atoms, preferably 3 or 4 carbon atoms. Examples of such unsaturated aliphatic acyl groups include the acryloyl, methacryloyl, crotonoyl, isocrotonoyl and propioloyl groups. Substituents on the substituted aliphatic acyl groups may be any of those defined generally as substituents (a) and exemplified herein. In the case of the aromatic acyl groups, the aromatic part is preferably as described above in relation to aryl groups and examples include arylcarbonyl groups and aralkyloxycarbonyl groups (wherein the aryl parts of said arylcarbonyl and aralkyloxycarbonyl groups are unsubstituted or have at least one substituent selected from the group consisting of halogen atoms, sulfamoyl groups, $C_1$–$C_4$ alkyl groups and $C_1$–$C_4$ alkoxy groups), such as the benzoyl, p-methoxybenzoyl, benzyloxycarbonyl and p-bromobenzyloxycarbonyl groups.

Where the substituent (a), $R^8$, $R^4$ or $R^5$ represents an alkoxycarbonyl group, the alkoxy part is a $C_1$–$C_6$ alkoxy group (examples of which are as given above) and may be a straight or branched chain group, and hence the alkoxycarbonyl group is a $C_2$–$C_7$ group. Preferred alkoxycarbonyl groups are the methoxycarbonyl and ethoxycarbonyl groups.

Where substituent (a), $R^6$, $R^7$ or substituent (b) represents a cycloalkyl group, this has from 3 to 7 ring carbon atoms and examples include the cyclopropyl, cyclobutyl, cyclopentyl, cyclohexyl and cycloheptyl groups.

Where substituent (a), $R^6$, $R^7$, substituent (b) or $R^6$ and $R^7$ together with the nitrogen atom to which they are attached represents a heterocyclic group, this is a group containing from 5 to 14 ring atoms, of which from 1 to 5 are selected from the group consisting of nitrogen, oxygen and sulfur atoms. The heterocyclic group more preferably has from 5 to 8 ring atoms, of which from 1 to 3 are said hetero-atoms. Most preferably, the heterocyclic group contains from 5 to 6 ring atoms, of which 1 or 2 are said hetero-atoms. The heterocyclic group may be aromatic in character or it may be non-aromatic and, if non-aromatic, its ring atoms may be fully saturated or it may include some unsaturated ring atoms.

Examples of such non-aromatic heterocyclic groups include the tetrahydrofuryl, tetrahydropyranyl, tetrahydrothiofuryl, tetrahydrothiopyranyl, aziridinyl, azetidinyl, pyrrolidinyl, piperidyl, hexahydroazepinyl, imidazolidinyl, oxazolidinyl, thiazolidinyl, morpholinyl (including morpholino), thiomorpholinyl (including thiomorpholino) and piperazinyl groups, any of which may be unsubstituted or substituted as defined above. As described more fully hereafter, there is no criticality as to the number of substituents on such substituted heterocyclic groups and examples of such substituents are as given herein. In the case of the non-aromatic heterocyclic groups, the preferred substituents are phenyl groups, substituted phenyl groups (wherein the substituents are at least one group or atom selected from the group consisting of halogen atoms, $C_1$–$C_4$ alkyl groups, $C_1$–$C_4$ alkoxy groups and trifluoromethyl groups), $C_1$–$C_4$ alkyl groups, substituted $C_1$–$C_4$ alkyl groups (wherein the substituents are at least one substituent selected from the group consisting of hydroxy groups, phenyl groups and substituted phenyl groups having at least one substituent selected from the group consisting of halogen atoms, $C_1$–$C_4$ alkyl groups, $C_1$–$C_4$ alkoxy groups and trifluoromethyl groups), $C_1$–$C_8$ alkanoyl groups, substituted $C_2$–$C_8$ alkanoyl groups (wherein the substituents are at least one substituent selected from the group consisting of heterocyclic groups, $C_3$–$C_7$ cycloalkyl groups, halogen atoms, $C_1$–$C_4$ alkoxy groups and phenyl groups), $C_2$–$C_5$ alkoxycarbonyl groups, aralkyloxycarbonyl groups (wherein the alkyl part is $C_1$–$C_4$ alkyl and the aryl part is $C_6$–$C_{10}$ aryl or $C_6$–$C_{10}$ aryl having at least one substituent selected from the group consisting of halogen, $C_1$–$C_4$ alkyl, $C_1$–$C_4$ alkoxy and trifluoromethyl substituents), $C_3$ and $C_4$ alkenoyl groups, benzoyl groups, substitueted benzoyl groups (wherein the substituent is at least one substituent selected from the group consisting of halogen atoms, sulfamoyl groups, $C_1$–$C_4$ alkyl groups and $C_1$–$C_4$ alkoxy groups), heterocyclic acyl groups, $C_1$–$C_4$ alkylsulfonyl groups, arylsulfonyl groups (wherein the aryl part is $C_6$–$C_{10}$ aryl or $C_6$–$C_{10}$ aryl having at least one substituent selected from the group consisting of halogen atoms, $C_1$–$C_4$ alkyl groups, $C_1$–$C_4$ alkoxy groups and trifluoromethyl groups), alkylcarbamoyl groups wherein the alkyl part is $C_1$–$C_4$ alkyl, heterocyclic groups, and oxygen atoms.

Where an oxygen atom is a substituent on a heterocyclic group, it may be attached to a ring carbon atom by covalent bonds, in which case it constitutes an "oxo" group (=O) or it may be attached by a coordinate bond to, for example, a sulfur atom (i.e. >S→O); of course, one or two oxygen atoms may be attached in this way to a ring sulfur atom.

Preferred examples of substituents on non-aromatic heterocyclic groups include the methyl, ethyl, phenyl, methoxycarbonyl, ethoxycarbonyl, benzyl, oxygen, hydroxyethyl, chlorophenyl, methoxyphenyl, trifluoromethylphenyl, pyridyl, benzhydryl, chlorobenzhydryl, difluorobenzhydryl, formyl, acetyl, valeryl, 3-butenoyl, chlorobutyryl, ethoxyacetyl, benzyloxycarbonyl, methanesulfonyl, toluenesulfonyl, benzoyl, chlorobenzoyl, methoxybenzoyl, nicotinoyl, isonicotinoyl, thenoyl, furoyl, methylcarbamoyl, p-chloro-m-sulfamoylbenzoyl, propionyl, isobutyryl, octanoyl, phenylpropionyl, cyclohexylpropionyl, heptanoyl and dimethoxybenzoyl groups.

In particular, we prefer, as substituted non-aromatic heterocyclic groups, the N-substituted piperazinyl groups and the optionally N-substituted 2,5-dimethyl-piperazinyl and 2,6-dimethyl-piperazinyl groups, wherein the N-substituents are selected from those defined above.

In the case of the aromatic heterocyclic groups, these preferably have 5 or 6 ring atoms, of which 1 or 2 are hetero-atoms selected from the group consisting of nitrogen, oxygen and sulfur atoms. Such groups may be unsubstituted or may have one or more of the substituents defined above; in the case of the aromatic heterocyclic groups, the preferred substituents are $C_1-C_4$ alkyl groups, particularly the methyl or ethyl groups. Examples of such substituted and unsubstituted aromatic heterocyclic groups include the furyl, thienyl, pyrrolyl, 1-methylpyrrolyl, pyridyl, 2-methylpyridyl, 3-ethylpyridyl, oxazolyl, thiazolyl and pyrimidinyl groups, of which the furyl, thienyl and pyridyl groups are preferred.

In the case of the above groups which are defined as "substituted", the number of such substituents is not critical to the present invention, but will, instead, be determined by the number of positions available for substitution and possibly also by steric constraints. For example, where the substituents are relatively small groups or atoms, the only restriction may be the number of positions available for substitution and it may be possible for all such positions to be substituted. On the other hand, if one or more of the substituents are relatively "bulky" groups, steric considerations apply and the number of such substituents may thereby be limited. However, this is well known to those skilled in the art and requires no further definition here.

A represents a $C_1-C_6$ alkylene group, i.e. a bivalent saturated aliphatic hydrocarbon group attached by one of its valences to the atom represented by "Q" and by the other of its valences to the group —$COR^3$. The free valences may be on different carbon atoms or they may be on the same carbon atom, in which case such a group is sometimes referred to as an "alkylidene" group. The alkylene group may be a straight or branched chain group. Examples of such alkylene groups include the methylene, ethylidene, ethylene, propylene, trimethylene, propylidene, tetramethylene, 1-methyltrimethylene, 2-methyltrimethylene, 3-methyltrimethylene, pentamethylene and hexamethylene groups, of which the methylene, ethylene, trimethylene and tetramethylene groups are preferred.

$R^1$ and $R^2$ may be hydrogen atoms or $C_1-C_6$ alkyl groups. We particularly prefer those compounds where one of $R^1$ and $R^2$ represents a hydrogen atom and the other represents a $C_1-C_6$ alkyl group, preferably a methyl group.

Examples of preferred classes of compound of the present invention are given below:

(1) Compounds of formula (I) and their salts, in which:
Q represents an oxygen atom;
A represents a $C_1-C_4$ alkylene group;
$R^3$ represents a $C_1-C_4$ alkoxy group, a 2,5-dialkylpyrrolyl group in which each alkyl part is $C_1-C_4$ alkyl or a group of formula —$(NH)_n NR^6 R^7$, wherein:
n is 0 or 1; and
$R^6$ and $R^7$ are independently selected from the group consisting of hydrogen atoms, $C_1-C_8$ alkyl groups, $C_3-C_6$ alkenyl groups, $C_5$ and $C_6$ cycloalkyl groups, phenyl groups, phenyl groups having at least one substituent selected from the group consisting of halogen, $C_1-C_4$ alkyl, $C_1-C_4$ alkoxy and trifluoromethyl substituents, heterocyclic groups having 5 or 6 ring atoms of which 1 or 2 are hetero-atoms selected from the group consisting of nitrogen, oxygen and sulfur atoms, substituted heterocyclic groups having 5 or 6 ring atoms of which 1 or 2 are hetero-atoms selected from the group consisting of nitrogen, oxygen and sulfur atoms and having at least one substituent selected from the group consisting of substituents (a) defined above, oxygen atoms, $C_1-C_6$ alkyl groups and $C_1-C_6$ alkyl groups having at least one substituent (a) defined above, and substituted $C_1-C_4$ alkyl groups having at least one substituent selected from the group consisting of:
(a') halogen atoms, hydroxy groups, $C_1-C_4$ alkoxy groups, dialkylamino groups wherein each alkyl group is $C_1-C_4$ alkyl, $C_2$ or $C_3$ alkoxycarbonyl groups, heterocyclic groups having 5 or 6 ring atoms of which 1 or 2 are hetero-atoms selected from the group consisting of nitrogen, oxygen and sulfur atoms, substituted heterocyclic groups having 5 or 6 ring atoms of which 1 or 2 are hetero-atoms selected from the group consisting of nitrogen, oxygen and sulfur atoms and having at least one substituent selected from the group consisting of substituents (a) defined above, oxygen atoms, $C_1-C_6$ alkyl groups and $C_1-C_6$ alkyl groups having at least one substituent (a) defined above, phenyl groups and phenyl groups having at least one substituent selected from the group consisting of halogen, $C_1-C_4$ alkyl, $C_1-C_4$ alkoxy and trifluoromethyl substituents;
$R^4$ and $R^5$ are independently selected from the group consisting of hydrogen atoms, $C_1-C_4$ alkyl groups, halogen atoms and nitro groups.

(2) Compounds of formula (I) and their salts, in which:
$R^1$ and $R^2$ are independently selected from the group consisting of hydrogen atoms and methyl groups;
Q represents an oxygen atom;
A represents a $C_1-C_4$ alkylene group;
$R^3$ represents a group of formula —$(NH)_n$—$NR^6 R^7$, wherein:

n is 0; and

R$^6$ and R$^7$ are independently selected from the group consisting of hydrogen atoms, C$_1$–C$_6$ alkyl groups, C$_5$ and C$_6$ cycloalkyl groups, 2,5-dimethylpyrrolyl groups, C$_3$ and C$_4$ alkenyl groups, heterocyclic groups having 5 or 6 ring atoms of which 1 or 2 are hetero-atoms selected from the group consisting of nitrogen, oxygen and sulfur atoms, substituted heterocyclic groups having 5 or 6 ring atoms of which 1 or 2 are hetero-atoms selected from the group consisting of nitrogen, oxygen and sulfur atoms and having at least one substituent selected from the group consisting of substituents (a) defined above, oxygen atoms, C$_1$–C$_6$ alkyl groups and C$_1$–C$_6$ alkyl groups having at least one substituent (a) defined above, and substituted C$_1$–C$_4$ alkyl groups having at least one substituent selected from the group consisting of:

(a″) C$_1$–C$_4$ alkoxy groups, C$_2$ and C$_3$ alkoxycarbonyl groups, morpholino groups, thiomorpholino groups, piperazinyl groups, homopiperazinyl groups, phenyl groups, phenyl groups having at least one substituent selected from the group consisting of halogen, C$_1$–C$_4$ alkyl, C$_1$–C$_4$ alkoxy and trifluoromethyl substituents, pyridyl groups and 1-piperazinyl groups having at the 4-position at least one substituent selected from the group consisting of:

(c) phenyl groups, phenyl groups having at least one substituent selected from the group consisting of halogen, C$_1$–C$_4$ alkyl, C$_1$–C$_4$ alkoxy and trifluoromethyl substituents, C$_1$–C$_4$ alkyl groups, substituted C$_1$–C$_4$ alkyl groups having at least one substituent selected from the group consisting of hydroxy substituents, phenyl substituents and phenyl substituents having at least one substituent selected from the group consisting of halogen, C$_1$–C$_4$ alkyl, C$_1$–C$_4$ alkoxy and trifluoromethyl substituents, formyl groups, C$_2$–C$_8$ alkanoyl groups, C$_2$–C$_5$ alkoxycarbonyl groups, aralkyloxycarbonyl groups wherein the alkyl part is C$_1$–C$_4$ alkyl and the aryl part is C$_6$–C$_{10}$ aryl or C$_6$–C$_{10}$ aryl having at least one substituent selected from the group consisting of halogen, C$_1$–C$_4$ alkyl, C$_1$–C$_4$ alkoxy and trifluoromethyl substituents, C$_3$ and C$_4$ alkenoyl groups, benzoyl groups, benzoyl groups having at least one substituent selected from the group consisting of halogen, sulfamoyl, C$_1$–C$_4$ alkyl and C$_1$–C$_4$ alkoxy substituents, heterocyclic acyl groups, C$_1$–C$_4$ alkylsulfonyl groups, arylsulfonyl groups wherein the aryl part is C$_6$–C$_{10}$ aryl or C$_6$–C$_{10}$ aryl having at least one substituent selected from the group consisting of halogen, C$_1$–C$_4$ alkyl, C$_1$–C$_4$ alkoxy and trifluoromethyl substituents, alkylcarbamoyl groups wherein the alkyl part is C$_1$–C$_4$ alkyl and substituted C$_2$–C$_6$ alkanoyl groups wherein the substituent is selected from the group consisting of halogen, C$_1$–C$_4$ alkoxy, C$_3$–C$_7$ cycloalkyl, phenyl and heterocyclic substituents;

R$^4$ represents a hydrogen atom; and

R$^5$ represents a hydrogen atom or a halogen, nitro or methyl group at the 3-position.

(3) Compounds of formula (I) and their salts, in which:

Q represents the oxygen atom;

A represents the methylene group;

R$^1$ represents the hydrogen atom;

R$^2$ represents the hydrogen atom or the methyl group;

R$^3$ represents a group of formula —NHR$^7$ and R$^7$ represents a C$_3$ or C$_4$ alkenyl group, a C$_1$–C$_6$ alkyl group, a heterocyclic group having 5 or 6 ring atoms of which 1 or 2 are nitrogen hetero-atoms, said heterocyclic group being unsubstituted or having at least one substituent selected from the group consisting of C$_1$–C$_4$ alkyl groups and phenylalkyl groups wherein the phenyl part is unsubstituted or itself has at least one substituent selected from the group consisting halogen, C$_1$–C$_4$ alkyl, C$_1$–C$_4$ alkoxy and trifluoromethyl substituents and wherein the alkyl part is C$_1$–C$_4$ alkyl, or a substituted C$_1$–C$_4$ alkyl group having at least one substituent selected from the group consisting of:

(a‴) C$_1$–C$_4$ alkoxy groups, morpholino groups, thiomorpholino groups, 1-piperazinyl groups, phenyl groups, phenyl groups having at least one substituent selected from the group consisting of halogen, alkyl and alkoxy substituents, pyridyl groups and 1-piperazinyl groups having at the 4-position a substituent selected from the group consisting of:

(c′) phenyl groups, phenyl groups having at least one substituent selected from the group consisting of halogen, C$_1$–C$_4$ alkyl, C$_1$–C$_4$ alkoxy and trifluoromethyl substituents, C$_1$–C$_4$ alkyl groups, C$_1$–C$_4$ alkyl groups having at least one substituent selected from the group consisting of hydroxy substituents, phenyl and substituents and phenyl substitutents having at least one substituent selected from halogen, C$_1$–C$_4$ alkyl, C$_1$–C$_4$ alkoxy and trifluoromethyl substituents, formyl groups, C$_2$–C$_5$ alkanoyl groups, C$_2$–C$_5$ alkanoyl groups having at least one substituent selected from the group consisting of C$_1$–C$_4$ alkoxy, halogen, phenyl, C$_3$–C$_7$ cycloalkyl and heterocyclic substitutents, C$_2$–C$_5$ alkoxycarbonyl groups, aralkyloxycarbonyl groups where the alkyl part is C$_1$–C$_3$ alkyl and the aryl part is phenyl or phenyl having at least one substituent selected from the group consisting of halogen, C$_1$–C$_4$ alkyl, C$_1$–C$_4$ alkoxy and trifluoromethyl substituents, C$_3$ and C$_4$ alkenoyl groups, benzoyl groups, benzoyl groups having at least one substituent selected from the group consisting of halogen, sulfamoyl, C$_1$–C$_4$ alkyl and C$_1$–C$_4$ alkoxy substituents, heterocyclic acyl groups wherein the heterocyclic part has 5 or 6 ring atoms of which 1 or 2 are hetero-atoms selected from the group consisting of nitrogen, oxygen and sulfur atoms, said heterocyclic group being unsubstituted or having at least one substituent selected from the group consisting of halogen, C$_1$–C$_4$ alkyl and C$_1$–C$_4$ alkoxy substituents, C$_1$–C$_4$ alkylsulfonyl groups, C$_6$–C$_{10}$ carbocyclic arylsulfonyl groups, C$_6$–C$_{10}$ carbocyclic arylsulfonyl groups having at least one substituent selected from the group consisting of halogen, $C_1-C_4$ alkyl, $C_1-C_4$ alkoxy and trifluoromethyl substituents, and alkylcarbamoyl groups where the alkyl part is $C_1-C_4$ alkyl;

$R^4$ represents a hydrogen atom; and $R^5$ represents a halogen atom or a methyl group at the 3-position.

The compounds of the invention contain basic nitrogen atoms and hence can form acid addition salts. The nature of such salts is not critical to the present invention, except that, where the salts are to be used for therapeutic purposes, they must be pharmaceutically acceptable which, as is well known to those skilled in the art, means that the salts must not have an increased toxicity, or an unacceptably increased toxicity, or a reduced activity, or unacceptably reduced activity, as compared with the free bases. A wide variety of acids may be employed to form such salts and representative examples of such acids include: mineral acids, such a hydrochloric acid, hydrobromic acid, hydroiodic acid, phosphoric acid, metaphosphoric acid, nitric acid or sulfuric acid; and organic acids, such as gastric acid, oxalic acid, tartaric acid, citric acid, benzoic acid, glycolic acid, gluconic acid, glucuronic acid, succinic acid, maleic acid or fumaric acid. Such acid addition salts may be prepared according to a conventional method.

Examples of certain compounds of the present invention are given in the following list and hereafter, where appropriate, the compounds of the invention are identified by the numbers assigned to them in this list. In the following list, those compounds identified by a number followed by the letter "a" are compounds in which there is a single carbon-carbon bond between the 4- and 5-positions of the pyridazine ring, whilst those compounds identified by a number followed by the letter "b" are compounds having a double bond between the 4- and 5-positions of the pyridazine ring.

In this list, the following abbreviations are used:

| | |
|---|---|
| Ac | acetyl |
| Boz | benzoyl |
| Bu | butyl |
| iBu | isobutyl |
| sBu | sec-butyl |
| Bz | benzyl |
| iByr | isobutyryl |
| Bzhy | benzhydryl |
| $c-C_3H_5$ | cyclopropyl |
| $c-C_4H_7$ | cyclobutyl |
| $c-C_5H_9$ | cyclopentyl |
| $c-C_6H_{11}$ | cyclohexyl |
| $c-C_7H_{13}$ | cycloheptyl |
| Diz | perhydro-1,4-diazepin-1-yl (= homopiperazinyl) |
| Et | ethyl |
| Fo | formyl |
| Fur | 2-furyl |
| Imid | 1-imidazolyl |
| Me | methyl |
| Mes | methanesulfonyl |
| Mor | morpholino |
| Octo | octanoyl |
| Ph | phenyl |
| Pip | piperidyl |
| Piz | 1-piperazinyl |
| Pr | propyl |
| iPr | isopropyl |
| Pyr | pyridyl |
| Pyrd | 1-pyrrolidinyl |
| Pyrr | 1-pyrrolyl |
| Thi | 2-thienyl |
| Thid | 1,3-thiazolin-3-yl |
| Thiz | 1,3-thiazolyl |
| Thz | perhydro-1,4-thiazin-4-yl (= thiomorpholino) |
| Tos | p-toluenesulfonyl |
| Va | valeryl |

Where a group identified by one of the above abbreviations can be attached to the remainder of the molecule through one of several of its atoms, the position of attachment is identified by the appropriate number preceding the abbreviation for that group; for example, in the case of the pyridyl group, this may be 3-Pyr, 2-Pyr etc. Also, where a group identified by one of the above abbreviations is substituted, the appropriate designation for its substituent or substituents precedes the abbreviation for the group so substituted and is itself (where appropriate) preceded by a number identifying the position of attachment of the substituent to the substituted group. For example, a 3-pyridyl group having an ethyl substituent at the 4-position would be identified as 4-Et-3-Pyr.

| Cpd No | $R^1$ | $R^2$ | $QAC(O)R^3$ | $R^4$ | $R^5$ |
|---|---|---|---|---|---|
| 1a/b | | H | $OCH_2COOH$ | 3-Cl | H |
| 2a/b | H | Me | $OCH_2COOH$ | 3-Cl | H |
| 3a/b | H | H | $OCH_2COOEt$ | H | H |
| 4a/b | H | Me | $OCH_2COOEt$ | H | H |
| 5a/b | H | H | $OCH_2COOEt$ | 2-Cl | H |
| 6a/b | H | H | $OCH_2COOEt$ | 3-Cl | H |
| 7a/b | Me | H | $OCH_2COOEt$ | 3-Cl | H |
| 8a/b | H | Me | $OCH_2COOEt$ | 3-Cl | H |
| 9a/b | H | H | $OCH_2COOEt$ | 3-Me | H |
| 10a/b | H | H | $OCH_2COOEt$ | 3-OMe | H |
| 11a/b | H | H | $OCH_2COOEt$ | $3-NO_2$ | H |
| 12a/b | H | H | $OCH_2COOEt$ | 2-Cl | 3-Cl |
| 13a/b | H | H | $OCH(Me)COOEt$ | 3-Cl | H |
| 14a/b | H | H | $OCH(Et)COOEt$ | 3-Cl | H |
| 15a/b | H | H | $O(CH_2)_3COOEt$ | 3-Cl | H |
| 16a/b | H | H | $OCH_2CONH_2$ | 3-Cl | H |
| 17a/b | H | Me | $OCH_2CONH_2$ | 3-Cl | H |
| 18a/b | H | H | $OCH_2CONHNH_2$ | 3-Cl | H |
| 19a/b | H | Me | $OCH_2CONHNH_2$ | 3-Cl | H |
| 20a/b | H | H | $OCH_2CONHMe$ | H | H |
| 21a/b | H | H | $OCH_2CONHMe$ | 3-Cl | H |
| 22a/b | H | Me | $OCH_2CONHMe$ | 3-Cl | H |
| 23a/b | H | H | $OCH_2CONHMe$ | 2-Cl | 3-Cl |
| 24a/b | H | H | $OCH(Me)CONHMe$ | 3-Cl | H |

-continued

| Cpd No | R¹ | R² | QAC(O)R³ | R⁴ | R⁵ |
|---|---|---|---|---|---|
| 25a/b | H | Me | OCH(Me)CONHMe | 3-Cl | H |
| 26a/b | H | H | OCH(Et)CONHMe | 3-Cl | H |
| 27a/b | H | H | OCH$_2$CONHEt | H | H |
| 28a/b | H | H | OCH$_2$CONHEt | 3-Cl | H |
| 29a/b | H | Me | OCH$_2$CONHEt | 3-Cl | H |
| 30a/b | H | H | OCH$_2$CONEt$_2$ | 3-Cl | H |
| 31a/b | H | Me | OCH$_2$CONEt$_2$ | 3-Cl | H |
| 32a/b | H | H | OCH$_2$CONHPr | H | H |
| 33a/b | H | Me | OCH$_2$CONHPr | 3-Cl | H |
| 34a/b | H | H | OCH$_2$CONHPr | 3-Cl | H |
| 35a/b | H | Me | OCH$_2$CONHPr | 3-F | H |
| 36a/b | H | Me | OCH$_2$CONHPr | H | H |
| 37a/b | H | H | OCH(Me)CONHPr | 3-Cl | H |
| 38a/b | H | H | OCH(Et)CONHPr | 3-Cl | H |
| 39a/b | H | H | OCH$_2$CONPr$_2$ | 3-Cl | H |
| 40a/b | H | H | OCH$_2$CONHiPr | 3-Cl | H |
| 41a/b | H | Me | OCH$_2$CONHiPr | 3-Cl | H |
| 42a/b | H | Me | OCH$_2$CONHiPr | H | H |
| 43a/b | H | H | OCH$_2$CONHBu | 3-Cl | H |
| 44a/b | H | Me | OCH$_2$CONHBu | 3-Cl | H |
| 45a/b | H | H | OCH$_2$CONBu$_2$ | 3-Cl | H |
| 46a/b | H | H | OCH$_2$CONHiBu | 3-Cl | H |
| 47a/b | H | Me | OCH$_2$CONHiBu | 3-Cl | H |
| 48a/b | H | H | OCH$_2$CONiBu$_2$ | 3-Cl | H |
| 49a/b | H | H | OCH$_2$CONHsBu | 3-Cl | H |
| 50a/b | H | H | OCH$_2$CON(Me)Bu | 3-Cl | H |
| 51a/b | H | H | OCH$_2$CONHC$_5$H$_{11}$ | 3-Cl | H |
| 52a/b | H | Me | OCH$_2$CONHC$_5$H$_{11}$ | 3-Cl | H |
| 53a/b | H | H | OCH$_2$CONHC$_6$H$_{13}$ | 3-Cl | H |
| 54a/b | H | Me | OCH$_2$CONHC$_6$H$_{13}$ | 3-Cl | H |
| 55a/b | H | H | OCH$_2$CONHC$_8$H$_{17}$ | 3-Cl | H |
| 56a/b | H | Me | OCH$_2$CONHC$_8$H$_{17}$ | 3-Cl | H |
| 57a/b | H | H | OCH$_2$CONHC$_9$H$_{19}$ | 3-Cl | H |
| 58a/b | H | H | OCH$_2$CONHCH$_2$CH$_2$Cl | 3-Cl | H |
| 59a/b | H | H | OCH$_2$CONH(CH$_2$)$_3$Cl | 3-Cl | H |
| 60a/b | H | Me | OCH$_2$CONH(CH$_2$)$_3$Cl | 3-Cl | H |
| 61a/b | H | Me | OCH$_2$CONHCH$_2$CH$_2$OMe | H | H |
| 62a/b | H | H | OCH$_2$CONHCH$_2$CH$_2$OMe | 3-Cl | H |
| 63a/b | H | H | OCH$_2$CONHCH$_2$CH$_2$OEt | 3-Cl | H |
| 64a/b | H | Me | OCH$_2$CONHCH$_2$CH$_2$OEt | 3-Cl | H |
| 65a/b | H | H | OCH$_2$CONHCH$_2$CH$_2$OEt | 3-Me | H |
| 66a/b | H | H | OCH$_2$CONH(CH$_2$)$_3$OMe | 3-Cl | H |
| 67a/b | H | Me | OCH$_2$CONH(CH$_2$)$_3$OMe | H | H |
| 68a/b | H | H | OCH$_2$CONHCH$_2$CH$_2$OH | 3-Cl | H |
| 69a/b | H | H | OCH$_2$CONHCH$_2$CH$_2$OH | 2-Cl | 3-Cl |
| 70a/b | H | H | OCH$_2$CONH(CH$_2$)$_4$OH | 3-Cl | H |
| 71a/b | H | H | OCH$_2$CONHCH$_2$CH$_2$OPh | 3-Cl | H |
| 72a/b | H | H | OCH$_2$CONHCH$_2$CH$_2$O(4-OMePh) | 3-Cl | H |
| 73a/b | H | H | OCH$_2$CONHCH$_2$CH$_2$NHMe | 3-Cl | H |
| 74a/b | H | H | OCH$_2$CONHCH$_2$CH$_2$NEt$_2$ | 3-Cl | H |
| 75a/b | H | H | OCH(Me)CONHCH$_2$CH$_2$NEt$_2$ | 3-Cl | H |
| 76a/b | H | H | OCH(Et)CONHCH$_2$CH$_2$NEt$_2$ | 3-Cl | H |
| 77a/b | H | H | OCH$_2$CONHCH$_2$CH$_2$N(Me)Ph | 3-Cl | H |
| 78a/b | H | H | OCH$_2$CONHCH$_2$COOH | 3-Cl | H |
| 79a/b | H | H | OCH$_2$CONHCH$_2$COOEt | 3-Cl | H |
| 80a/b | H | H | OCH$_2$CONHCH(CH$_2$Ph)COOEt | 3-Cl | H |
| 81a/b | H | H | OCH$_2$CONHCH$_2$-c-C$_6$H$_{11}$ | 3-Cl | H |
| 82a/b | H | H | OCH$_2$CONHCH$_2$CH$_2$-c-C$_6$H$_{11}$ | 3-Cl | H |
| 83a/b | H | H | OCH$_2$CONHCH$_2$Ph | 3-Cl | H |
| 84a/b | H | H | OCH$_2$CONHCH$_2$(2-OMePh) | 3-F | H |
| 85a/b | H | H | OCH$_2$CONHCH$_2$(2-OMePh) | 3-Cl | H |
| 86a/b | H | H | OCH$_2$CONHCH$_2$(3-OMePh) | 3-Cl | H |
| 87a/b | H | H | OCH$_2$CONHCH$_2$(4-OMePh) | 3-Cl | H |
| 88a/b | H | H | OCH$_2$CONHCH$_2$(4-ClPh) | 3-Cl | H |
| 89a/b | H | H | OCH$_2$CONHCH$_2$(2,4-diClPh) | 3-Cl | H |
| 90a/b | H | H | OCH$_2$CON(Et)CH$_2$Ph | 3-Cl | H |
| 91a/b | H | H | OCH$_2$CONHCH$_2$CH$_2$Ph | 3-Cl | H |
| 92a/b | H | Me | OCH$_2$CONHCH$_2$CH$_2$Ph | 3-Cl | H |
| 93a/b | H | H | OCH$_2$CONHCH$_2$CH$_2$Ph | 3-F | H |
| 94a/b | H | Me | OCH$_2$CONHCH$_2$CH$_2$Ph | 3-F | H |
| 95a/b | H | Me | OCH$_2$CONHCH$_2$CH$_2$Ph | 3-Me | H |
| 96a/b | H | H | OCH$_2$CONHCH$_2$CH$_2$(4-OMePh) | 3-Cl | H |
| 97a/b | H | Me | OCH$_2$CONHCH$_2$CH$_2$(4-OMePh) | 3-Cl | H |
| 98a/b | H | H | OCH$_2$CONHCH$_2$CH$_2$(4-OMePh) | 3-F | H |
| 99a/b | H | Me | OCH$_2$CONHCH$_2$CH$_2$(4-OMePh) | 3-F | H |
| 100a/b | H | H | OCH$_2$CONHCH$_2$CH$_2$(2-OMePh) | 3-Cl | H |
| 101a/b | H | Me | OCH$_2$CONHCH$_2$CH$_2$(2-OMePh) | 3-Cl | H |
| 102a/b | H | Me | OCH$_2$CONHCH$_2$CH$_2$(2-OMePh) | 3-Br | H |
| 103a/b | H | Me | OCH$_2$CONHCH$_2$CH$_2$(2-OMePh) | 3-F | H |
| 104a/b | H | H | OCH$_2$CONHCH$_2$CH$_2$(3,4-diOMePh) | 2-Cl | H |

-continued

| Cpd No | R¹ | R² | QAC(O)R³ | R⁴ | R⁵ |
|---|---|---|---|---|---|
| 105a/b | H | H | OCH₂CONHCH₂CH₂(3,4-diOMePh) | 3-Cl | H |
| 106a/b | H | Me | OCH₂CONHCH₂CH₂(3,4-diOMePh) | 3-Cl | H |
| 107a/b | Me | H | OCH₂CONHCH₂CH₂(3,4-diOMePh) | 3-Cl | H |
| 108a/b | H | H | OCH₂CONHCH₂CH₂(3,4-diOMePh) | 3-Cl | 5-Cl |
| 109a/b | H | H | OCH₂CONHCH₂CH₂(3,4-diOMePh) | 3-F | H |
| 110a/b | H | Me | OCH₂CONHCH₂CH₂(3,4-diOMePh) | 3-F | H |
| 111a/b | H | H | OCH₂CONHCH₂CH₂(3,4-diOMePh) | 3-Me | H |
| 112a/b | H | Me | OCH₂CONHCH₂CH₂(3,4-diOMePh) | 3-Me | H |
| 113a/b | H | H | OCH₂CONHCH₂CH₂(3,4-diOMePh) | 3-NO₂ | H |
| 114a/b | H | H | OCH₂CONHCH₂CH₂(3,4-diOMePh) | 3-CN | H |
| 115a/b | H | H | OCH₂CONHCH₂CH₂(4-ClPh) | 3-Cl | H |
| 116a/b | H | Me | OCH₂CONHCH₂CH₂(4-ClPh) | 3-Cl | H |
| 117a/b | H | Me | OCH₂CONHCH₂CH₂(4-ClPh) | 3-F | H |
| 118a/b | H | Me | OCH₂CONHCH₂CH₂(2-ClPh) | 3-Cl | H |
| 119a/b | H | Me | OCH₂CONHCH₂CH₂(4-MePh) | 3-Cl | H |
| 120a/b | H | H | OCH₂CONH(CH₂)₃Ph | 3-Cl | H |
| 121a/b | H | Me | OCH₂CONH(CH₂)₃Ph | 3-Cl | H |
| 122a/b | H | H | OCH₂CONH(CH₂)₄Ph | 3-Cl | H |
| 123a/b | H | Me | OCH₂CONH(CH₂)₄Ph | 3-Cl | H |
| 124a/b | H | H | OCH₂CONHCH₂(4-Pyr) | 3-Cl | H |
| 125a/b | H | H | OCH₂CONHCH₂CH₂(2-Pyr) | H | H |
| 126a/b | H | H | OCH₂CONHCH₂CH₂(2-Pyr) | 2-Cl | H |
| 127a/b | H | H | OCH₂CONHCH₂CH₂(2-Pyr) | 3-Cl | H |
| 128a/b | Me | H | OCH₂CONHCH₂CH₂(2-Pyr) | 3-Cl | H |
| 129a/b | H | Me | OCH₂CONHCH₂CH₂(2-Pyr) | 3-Cl | H |
| 130a/b | H | Me | OCH₂CONHCH₂CH₂(2-Pyr) | H | H |
| 131a/b | H | H | OCH₂CONHCH₂CH₂(2-Pyr) | 3-F | H |
| 132a/b | H | Me | OCH₂CONHCH₂CH₂(2-Pyr) | 3-F | H |
| 133a/b | H | H | OCH₂CONHCH₂CH₂(2-Pyr) | 3-NO₂ | H |
| 134a/b | H | H | O(CH₂)₃CONHCH₂CH₂(2-Pyr) | 3-Cl | H |
| 135a/b | H | H | OCH₂CONHCH₂CH:CH₂ | 3-Cl | H |
| 136a/b | H | Me | OCH₂CONHCH₂CH:CH₂ | 3-Cl | H |
| 137a/b | H | H | OCH₂CONHCH₂CMe:CH₂ | 3-Cl | H |
| 138a/b | H | H | OCH₂CONH-c-C₆H₁₁ | 3-Cl | H |
| 139a/b | H | H | OCH₂CONH(4-OMePh) | 3-Cl | H |
| 140a/b | H | H | OCH₂CONHNHPh | 3-Cl | H |
| 141a/b | H | H | OCH₂CONH(2-Pyr) | 3-Cl | H |
| 142a/b | H | H | OCH₂CONH(2-Thiz) | 3-Cl | H |
| 143a/b | H | H | OCH₂CONH(2,5-diMePyrr) | 3-Cl | H |
| 144a/b | H | Me | OCH₂CONH(2,5-diMePyrr) | 3-Cl | H |
| 145a/b | H | H | OCH₂CONH(1-Bz-4-Pip) | 3-Cl | H |
| 146a/b | H | H | OCH₂CONH(1-Me-4-Pip) | 3-Cl | H |
| 147a/b | H | H | OCH₂CO(1-Pip) | 3-Cl | H |
| 148a/b | H | H | OCH₂CONH(1-Pip) | 3-Cl | H |
| 149a/b | H | H | OCH₂CONHMor | 3-Cl | H |
| 150a/b | H | H | OCH₂CO(4-MePiz) | 3-Cl | H |
| 151a/b | H | H | OCH₂CO(4-PhPiz) | 3-Cl | H |
| 152a/b | H | H | OCH₂CO(4-COOEtPiz) | 3-Cl | H |
| 153a/b | H | Me | OCH₂CONHNHCOMe | 3-Cl | H |
| 154a/b | H | H | OCH₂CONHNHCO(CH₂)₃Cl | 3-Cl | H |
| 155a/b | H | H | OCH₂CONHNHCO(CH₂)₃OEt | 3-Cl | H |
| 156a/b | H | H | OCH₂CONHNHCOCH₂-c-C₆H₁₁ | 3-Cl | H |
| 157a/b | H | H | OCH₂CONHNHCOCH₂CH₂Ph | 3-Cl | H |
| 158a/b | H | H | OCH₂CONHNHCOCH:CHPh | 3-Cl | H |
| 159a/b | H | H | OCH₂CONHN=CHCH₂Cl | 3-Cl | H |
| 160a/b | H | H | OCH₂CONHN=CH(4-OMePh) | 3-Cl | H |
| 161a/b | H | H | OCH₂CONHCH₂CH₂Imid | 3-Cl | H |
| 162a/b | H | Me | OCH₂CONHCH₂CH₂Imid | 3-Cl | H |
| 163a/b | H | H | OCH₂CONHCH₂CH₂(4-Pyr) | 3-Cl | H |
| 164a/b | H | Me | OCH₂CONHCH₂CH₂(4-Pyr) | 3-Cl | H |
| 165a/b | H | H | SCH₂CONHCH₂CH₂Mor | H | H |
| 166a/b | H | H | OCH₂CONHCH₂CH₂Mor | H | H |
| 167a/b | H | H | OCH₂CONHCH₂CH₂Mor | 3-Cl | H |
| 168a/b | H | Me | OCH₂CONHCH₂CH₂Mor | 3-Cl | H |
| 169a/b | Me | H | OCH₂CONHCH₂CH₂Mor | 3-Cl | H |
| 170a/b | H | H | OCH₂CONHCH₂CH₂Mor | 3-Cl | 5-Cl |
| 171a/b | H | H | OCH₂CONHCH₂CH₂Mor | 2-Cl | H |
| 172a/b | H | H | OCH₂CONHCH₂CH₂Mor | 3-F | H |
| 173a/b | H | Me | OCH₂CONHCH₂CH₂Mor | 3-F | H |
| 174a/b | H | H | OCH₂CONHCH₂CH₂Mor | 3-NO₂ | H |
| 175a/b | H | H | OCH₂CONHCH₂CH₂Mor | 3-Me | H |
| 176a/b | H | Me | OCH₂CONHCH₂CH₂Mor | 3-Me | H |
| 177a/b | H | H | OCH₂CONHCH₂CH₂Mor | 3-NHAc | H |
| 178a/b | H | H | OCH₂CONHCH₂CH₂Mor | 3-CN | H |
| 179a/b | H | H | OCH₂CONHCH₂CH₂Mor | 3-CONH₂ | H |
| 180a/b | H | H | OCH₂CONHCH₂CH₂(2,6-diMeMor) | 3-Cl | H |
| 181a/b | H | H | OCH₂CONH(CH₂)₃Mor | 3-Cl | H |
| 182a/b | H | Me | OCH₂CONH(CH₂)₃Mor | 3-Cl | H |
| 183a/b | H | H | O(CH₂)₃CONHCH₂CH₂Mor | 3-Cl | H |
| 184a/b | H | H | OCH₂CONHNHCH₂CH₂Mor | 3-Cl | H |

-continued

| Cpd No | R¹ | R² | QAC(O)R³ | R⁴ | R⁵ |
|---|---|---|---|---|---|
| 185a/b | H | Me | OCH₂CONHNHCH₂CH₂Mor | 3-Cl | H |
| 186a/b | H | H | OCH₂CONHCH₂CH₂NHMor | 3-Cl | H |
| 187a/b | H | H | OCH₂CONHCH₂CH₂Thz | 3-Cl | H |
| 188a/b | H | Me | OCH₂CONHCH₂CH₂Thz | 3-Cl | H |
| 189a/b | H | H | 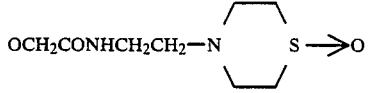 OCH₂CONHCH₂CH₂—N⟨ ⟩S→O | 3-Cl | H |
| 190a/b | H | H | OCH₂CONHCH₂CH₂(1,1-diO-Thz) | 3-Cl | H |
| 191a/b | H | H | OCH₂CONHCH₂CH₂Thz | 3-Me | H |
| 192a/b | H | H | OCH₂CONHCH₂CH₂(Thid) | 3-Cl | H |
| 193a/b | H | H | OCH₂CONHCH₂CH₂(1-Pip) | 3-Cl | H |
| 194a/b | H | H | OCH₂CONHNHCH₂CH₂(1-Pip) | 3-Cl | H |
| 195a/b | H | Me | OCH₂CONHNHCH₂CH₂(1-Pip) | 3-Cl | H |
| 196a/b | H | H | OCH₂CONHCH₂CH₂NH(1-Pip) | 3-Cl | H |
| 197a/b | H | H | OCH₂CONHCH₂CH₂Pyrd | 3-Cl | H |
| 198a/b | H | H | OCH₂CONHNHCH₂CH₂Pyrd | 3-Cl | H |
| 199a/b | H | Me | OCH₂CONHNHCH₂CH₂Pyrd | 3-Cl | H |
| 200a/b | H | H | OCH₂CONHCH₂CH₂NHPyrd | 3-Cl | H |
| 201a/b | H | H | OCH₂CONHCH₂COMor | 3-Cl | H |
| 202a/b | H | H | OCH₂CONHCH₂CH₂(4-MePiz) | 3-Cl | H |
| 203a/b | H | Me | OCH₂CONHCH₂CH₂(4-MePiz) | 3-Cl | H |
| 204a/b | H | H | OCH₂CONHCH₂CO(4-MePiz) | 3-Cl | H |
| 205a/b | H | H | OCH₂CONHCH₂CH₂-[4-(2-OHEt)Piz] | 3-Cl | H |
| 206a/b | H | H | OCH₂CONHCH₂CH₂(4-PhPiz) | 3-Cl | H |
| 207a/b | H | Me | OCH₂CONHCH₂CH₂(4-PhPiz) | 3-Cl | H |
| 208a/b | H | H | OCH₂CONHCH₂CO(4-PhPiz) | 3-Cl | H |
| 209a/b | H | H | OCH₂CONHCH₂CH₂-[4-(2-ClPh)Piz] | 3-Cl | H |
| 210a/b | H | H | OCH₂CONHCH₂CH₂-[4-(3-ClPh)Piz] | 3-Cl | H |
| 211a/b | H | H | OCH₂CONHCH₂CH₂-[4-(4-ClPh)Piz] | 3-Cl | H |
| 212a/b | H | H | OCH₂CONHCH₂CH₂-[4-(2-OMePh)Piz] | 3-Cl | H |
| 213a/b | H | Me | OCH₂CONHCH₂CH₂-[4-(2-OMePh)Piz] | 3-Cl | H |
| 214a/b | H | H | OCH₂CONHCH₂CH₂-[4-(3-OMePh)Piz] | 3-Cl | H |
| 215a/b | H | Me | OCH₂CONHCH₂CH₂-[4-(3-OMePh)Piz] | 3-Cl | H |
| 216a/b | H | H | OCH₂CONHCH₂CH₂-[4-(4-OMePh)Piz] | 3-Cl | H |
| 217a/b | H | Me | OCH₂CONHCH₂CH₂-[4-(4-OMePh)Piz] | 3-Cl | H |
| 218a/b | H | H | OCH₂CONHCH₂CH₂-[4-(3-MePh)Piz] | 3-Cl | H |
| 219a/b | H | H | OCH₂CONHCH₂CH₂-[4-(3-CF₃Ph)Piz] | 3-Cl | H |
| 220a/b | H | H | OCH₂CONHCH₂CH₂Piz | 3-Cl | H |
| 221a/b | H | Me | OCH₂CONHCH₂CH₂Piz | 3-Cl | H |
| 222a/b | H | H | OCH₂CONHCH₂CH₂Diz | 3-Cl | H |
| 223a/b | H | H | OCH₂CONHCH₂CH₂-(3,5-diMePiz) | 3-Cl | H |
| 224a/b | H | H | OCH₂CONHCH₂CH₂-(4-2-PyrPiz) | 3-Cl | H |
| 225a/b | H | Me | OCH₂CONHCH₂CH₂(4-2-PyrPiz) | 3-Cl | H |
| 226a/b | H | H | OCH₂CONHCH₂CO(4-2-PyrPiz) | 3-Cl | H |
| 227a/b | H | H | OCH₂CONHCH₂CH₂(4-BzhyPiz) | 3-Cl | H |
| 228a/b | H | H | OCH₂CONHCH₃CH₂-(4-p-ClBzhyPiz) | 3-Cl | H |
| 229a/b | H | H | OCH₂CONHCH₂CH₂-(4-p,p-diFBzhyPiz) | 3-Cl | H |
| 230a/b | H | H | OCH₂CONHCH₂CH₂-(4-p,p-diFBzhyPiz) | H | H |
| 231a/b | H | Me | OCH₂CONHCH₂CH₂-(4-p,p-diFBzhyPiz) | 3-Cl | H |
| 232a/b | H | H | OCH₂CONHCH₂CH₂-[4-Bzhy(CH₂)₃Piz] | 3-Cl | H |
| 233a/b | H | H | OCH₂CONHCH₂CH₂(4-BzPiz) | 3-Cl | H |
| 234a/b | H | Me | OCH₂CONHCH₂CH₂(4-BzPiz) | 3-Cl | H |
| 235a/b | H | H | OCH₂CONHCH₂CH₂(4-FoPiz) | 3-Cl | H |
| 236a/b | H | H | OCH₂CONHCH₂CH₂(4-AcPiz) | 3-Cl | H |
| 237a/b | H | H | OCH₂CONHCH₂CH₂(4-VaPiz) | 3-Cl | H |
| 238a/b | H | H | OCH₂CONHCH₂CH₂-(4-CH₂:CHCH₂CO-Piz) | 3-Cl | H |
| 239a/b | H | H | OCH₂CONHCH₂CH₂-[4-Cl(CH₂)₃CO-Piz] | 3-Cl | H |
| 240a/b | H | H | OCH₂CONHCH₂CH₂-(4-EtOCH₂CO-Piz) | 3-Cl | H |
| 241a/b | H | H | OCH₂CONHCH₂CH₂-(4-COOEt-Piz) | 3-Cl | H |
| 242a/b | H | H | OCH₂CONHCH₂CH₂-(4-BzOCO-Piz) | 3-Cl | H |
| 243a/b | H | H | OCH₂CONHCH₂CH₂(4-MesPiz) | 3-Cl | H |
| 244a/b | H | H | OCH₂CONHCH₂CH₂(4-TosPiz) | 3-Cl | H |
| 245a/b | H | H | OCH₂CONHCH₂CH₂(4-BozPiz) | 3-Cl | H |
| 246a/b | H | H | OCH₂CONHCH₂CH₂-(4-p-ClBozPiz) | 3-Cl | H |
| 247a/b | H | H | OCH₂CONHCH₂CH₂-(4-p-OMeBozPiz) | 3-Cl | H |
| 248a/b | H | H | OCH₂CONHCH₂CH₂-[4-(3-PyrCO)Piz] | 3-Cl | H |
| 249a/b | H | H | OCH₂CONHCH₂CH₂(4-ThiCOPiz) | 3-Cl | H |
| 250a/b | H | H | OCH₂CONHCH₂CH₂(4-FurCOPiz) | 3-Cl | H |
| 251a/b | H | H | OCH₂CONHCH₂CH₂(4-CONHMe-Piz) | 3-Cl | H |
| 252a/b | H | H | OCH₂CONHCH₂CH₂-[4-(p-Cl-m-NH₂SO₂-Boz)Piz] | 3-Cl | H |
| 253a/b | H | Me | OCH₂CONHCH₂CH₂-[4-(p-Cl-m-NH₂SO₂-Boz)Piz] | 3-Cl | H |
| 254a/b | H | Me | OCH₂CONHNH(p-Cl-m-NH₂SO₂-Boz) | 3-Cl | H |
| 255a/b | H | H | OCH₂COOBu | 3-Cl | H |
| 256a/b | H | H | OCH₂COOPh | 3-Cl | H |
| 257a/b | H | H | OCH₂COOCH₂Ph | 3-Cl | H |
| 258a/b | H | Me | OCH₂CONiBu₂ | 3-Cl | H |
| 259a/b | H | H | OCH₂CON(C₅H₁₁)₂ | 3-Cl | H |
| 260a/b | H | H | OCH₂CON(C₆H₁₃)₂ | 3-Cl | H |

-continued

| Cpd No | R¹ | R² | QAC(O)R³ | R⁴ | R⁵ |
|---|---|---|---|---|---|
| 261a/b | H | H | OCH$_2$CON(CH$_2$CH:CH$_2$)$_2$ | 3-Cl | H |
| 262a/b | H | H | OCH$_2$CONHCH(COOH)CH$_2$Ph | 3-Cl | H |
| 263a/b | H | H | OCH$_2$CONHCH$_2$CH$_2$OPr | 3-Cl | H |
| 264a/b | H | H | OCH$_2$CONH(CH$_2$)$_3$OPr | 3-Cl | H |
| 265a/b | H | Me | OCH$_2$CONHCH$_2$CH$_2$(3,4,5-triOMePh) | 3-Cl | H |
| 266a/b | H | H | OCH$_2$CONHCH$_2$Fur | 3-Cl | H |
| 267a/b | H | H | OCH$_2$CONHFur | 3-Cl | H |
| 268a/b | H | H | OCH$_2$CONHCH$_2$Thi | 3-Cl | H |
| 269a/b | H | H | OCH$_2$CONHThi | 3-Cl | H |
| 270a/b | H | H | OCH$_2$CONHCH$_2$CONHC$_3$H$_7$ | 3-Cl | H |
| 271a/b | H | H | OCH$_2$CONHCH$_2$CO(4-COOEtPiz) | 3-Cl | H |
| 272a/b | H | Me | OCH$_2$CONHCH$_2$CH$_2$Cl | 3-Cl | H |
| 273a/b | H | Me | OCH$_2$CONHCH$_2$CH$_2$(4-AcPiz) | 3-Cl | H |
| 274a/b | H | H | OCH$_2$CONHCH$_2$CH$_2$(4-COCH$_2$CH$_3$Piz) | 3-Cl | H |
| 275a/b | H | H | OCH$_2$CONHCH$_2$CH$_2$(4-COCH$_2$CH$_3$Piz) | 3-Me | H |
| 276a/b | H | H | OCH$_2$CONHCH$_2$CH$_2$(4-COCH$_2$CH$_3$Piz) | 3-NO$_2$ | H |
| 277a/b | H | H | OCH$_2$CONHCH$_2$CH$_2$(4-iByrPiz) | 3-Cl | H |
| 278a/b | H | Me | OCH$_2$CONHCH$_2$CH$_2$(4-iByrPiz) | 3-Cl | H |
| 279a/b | H | H | OCH$_2$CONHCH$_2$CH$_2$(4-iByrPiz) | 3-Me | H |
| 280a/b | H | H | OCH$_2$CONHCH$_2$CH$_2$(4-iByrPiz) | 3-F | H |
| 281a/b | H | H | OCH$_2$CONHCH$_2$CH$_2$(4-OctoPiz) | 3-Cl | H |
| 282a/b | H | H | OCH$_2$CONHCH$_2$CH$_2$-(4-PhCH$_2$CH$_2$CO-Piz) | 3-Cl | H |
| 283a/b | H | Me | OCH$_2$CONHCH$_2$CH$_2$-(4-PhCH$_2$CH$_2$CO-Piz) | 3-Cl | H |
| 284a/b | H | H | OCH$_2$CONHCH$_2$CH$_2$-(4-c-C$_6$H$_{11}$CH$_2$CH$_2$CO-Piz) | 3-Cl | H |
| 285a/b | H | Me | OCH$_2$CONHPr | 3-Me | H |
| 286a/b | H | Me | OCH$_2$CONHBu | 3-Me | H |
| 287a/b | H | Me | OCH$_2$CONHiBu | 3-Me | H |
| 288a/b | H | Me | OCH$_2$CONHC$_5$H$_{11}$ | 3-Me | H |
| 289a/b | H | Me | OCH$_2$CONHC$_6$H$_{13}$ | 3-Me | H |
| 290a/b | H | Me | OCH$_2$CONHCH$_2$CH$_2$(4-MePiz) | 3-Me | H |
| 291a/b | H | Me | OCH$_2$CONHCH$_2$CH$_2$(4-ClPh) | 3-Me | H |
| 292a/b | H | Me | OCH$_2$CONHCH$_2$CH$_2$(4-PhPiz) | 3-Me | H |
| 293a/b | H | Me | OCH$_2$CONHCH$_2$CH$_2$(2-Pyr) | 3-Me | H |
| 294a/b | H | Me | OCH$_2$CONHCH$_2$CH$_2$(4-2-PyrPiz) | 3-Me | H |
| 295a/b | H | H | OCH$_2$CONHCH$_2$CH:CH$_2$ | 3-Me | H |
| 296a/b | H | H | OCH$_2$CONHiBu | 3-Me | H |
| 297a/b | H | H | OCH$_2$CONHCH$_2$CH$_2$(4-COOEtPiz) | 3-Me | H |
| 298a/b | H | H | OCH$_2$CONHCH$_2$CH$_2$(2-Pyr) | 3-Me | H |
| 299a/b | H | H | OCH$_2$CONHCH$_2$CH$_2$-(4-p,p-diFBzhyPiz) | 3-Me | H |
| 300a/b | H | H | OCH$_2$CONH(CH$_2$)$_3$Mor | 3-Me | H |
| 301a/b | H | H | OCH$_2$CONHCH$_2$CH$_2$(4-MePiz) | 3-Me | H |
| 302a/b | H | H | OCH$_2$CONHCH$_2$CH$_2$(4-PhPiz) | 3-Me | H |
| 303a/b | H | H | OCH$_2$CONHCH$_2$CH$_2$-(4-2-PyrPiz) | 3-Me | H |
| 304a/b | H | H | OCH$_2$CONHCH$_2$CH$_2$4-AcPiz) | 3-Me | H |
| 305a/b | H | H | OCH$_2$CONH(1-Bz-4-Pip) | 3-Me | H |
| 306a/b | H | H | OCH$_2$CONHCH$_2$CH$_2$-(4-COC$_6$H$_{13}$Piz) | 3-Cl | H |
| 307a/b | H | H | OCH$_2$CONHCH$_2$CH$_2$-(4-3,5-diOMeBozPiz) | 3-Cl | H |

Of the compounds listed above, preferred compounds are Compounds Nos. 33a, 44a, 46a, 47a, 52a, 54a, 63a, 92a, 96b, 106a, 109a, 111a, 116a, 127a, 129a, 135a, 145a, 167a, 167b, 168a, 172a, 175a, 181a, 202a, 206a, 224a, and 236a, as well as pharmaceutically acceptable acid addition salts of these compounds.

The compounds of the invention may be prepared by a variety of methods, for example as illustrated below.

Method A

The compounds of the invention may be prepared from the corresponding 6-(4-hydroxy- or mercapto-phenyl) pyridazinone compounds as illustrated in the following reaction scheme:

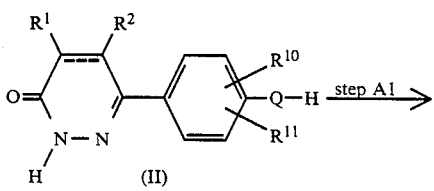

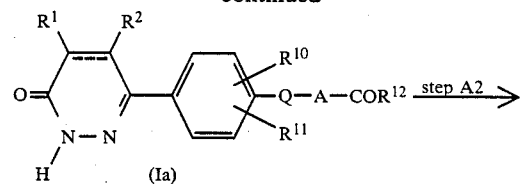

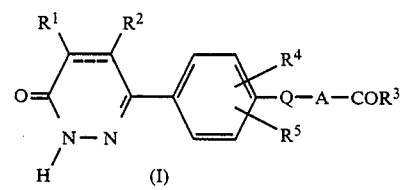

In the above formulae, R¹, R², R³, R⁴, R⁵, Q, A and the dotted lines are as defined above. R¹⁰ and R¹¹ are the same or different and each represents a hydrogen atom, a C$_1$-C$_6$ alkyl group, a C$_1$-C$_6$ alkyl group having at least one halogen substituent, a halogen atom, a C$_1$-C$_6$ alkoxy group, a C$_1$-C$_7$ aliphatic carboxylic acyloxy group, a protected amino group, a protected monoalkylamino group where the alkyl group is C$_1$-C$_6$ alkyl, a dialkylamino group where each alkyl group is $C_1$-$C_6$ alkyl, a $C_1$-$C_7$ aliphatic carboxylic acylamino group, a $C_1$-$C_7$ aliphatic acyl group, a carboxy group, a carbamoyl group, a carbamoyl group having 1 to 2 $C_1$-$C_6$ alkyl substituents, a ureido group, an alkylureido group wherein the alkyl group is $C_1$-$C_6$ alkyl, a thioureido group, an alkylthioureido group wherein the alkyl group is $C_1$-$C_6$ alkyl, a cyano group or a nitro group.

$R^{12}$ represents any one of the groups represented by $R^3$, but, in this case, any active groups or atoms therein may be protected. Also, in the case of certain groups which may be represented by $R^3$, it may be convenient (albeit not essential) to prepare first a compound containing a different group and then convert it to another group by one of the optional reactions of step A2.

Examples of the groups which may be represented by $R^{10}$, $R^{11}$ and $R^{12}$ are given above.

In step A1 of Method A, a compound of formula (II) is converted to an alkali metal salt thereof and then reacted with a halo compound of formula (V):

$$AX-COR^{12} \qquad (V)$$

(in which $R^{12}$ and A are as defined above, and X represents a halogen atom, for example a chlorine, bromine or iodine atom).

The reaction is preferably effected in the presence of a solvent, the nature of which is not critical, provided that it has no adverse effect upon the reaction. Suitable solvents include, for example: amides, such as dimethylformamide, dimethylacetamide or hexamethylphosphoric triamide; sulfoxides, such as dimethyl sulfoxide; and nitriles, such as acetonitrile.

The alkali metal salt to which the compound of formula (II) is converted is preferably a sodium, potassium or lithium salt. Conversion to this salt may be effected by treating the compound of formula (II) with an alkali metal compound, for example: an alkali metal hydride, such as sodium hydride or potassium hydride; or an organic lithium compound, such as lithium isobutyl cyclohexylamide or lithium dicyclohexylamide. This reaction may be effected over a wide range of temperatures, but suitably at a relatively low temperature, for example from $-20°$ C. to about ambient temperature. The reaction to produce the alkali metal salt will normally require a period of from 30 minutes to 2 hours.

Reaction of the alkali metal salt of the compound of formula (II) with the compound of formula (V) is preferably effected in one of the above solvents at a temperature of from 0° C. to 120° C. The time required for the reaction will vary widely, depending upon many factors, primarily the reaction temperature, but a period of from 30 minutes to 5 hours will normally suffice.

The relative proportions of the alkali metal salt of the compound of formula (II) and the compound of formula (V) may vary widely, although approximately stoichiometric amounts are preferred. Although the reaction may be accelerated by employing an excess of the compound of formula (V), this can result in the introduction of a group of formula —A—$COR^{12}$ as a substituent on the nitrogen atom at the 2-position of the pyridazinone system.

After completion of the reaction, the resulting compound of formula (Ia) may be recovered from the reaction mixture by conventional means. For example, one suitable recovery technique comprises: distilling the solvent from the reaction mixture; mixing the residue with ice-water; extracting the mixture with a water-immiscible organic solvent; washing with water and then drying the extract; and finally distilling the solvent from the extract to give the desired product. If desired, this may be further purified by conventional techniques, for example recrystallization or the various chromatography techniques, particularly column chromatography.

The compounds of formula (II) employed as starting materials in this process are either already known or may be prepared by known methods, for example as described in the Journal of Medicinal Chemistry, 17, 273 (1974) or by a method similar to that described in steps B1 and B2 of Method B.

The reactions represented by step A2 in the above reaction scheme are optional and include the following series of reactions, which, where two or more are to be employed, may be selected and combined in any appropriate order:

hydrolysis of any ester group (e.g. an aliphatic acyloxy group, an alkoxycarbonyl group, an aryloxycarbonyl group or an aralkyloxycarbonyl group);

conversion of a carboxy group, an alkoxycarbonyl group, an aryloxycarbonyl group or an aralkyloxycarbonyl group to an optionally substituted hydrazinocarbonyl or carbamoyl group;

conversion of a nitro group into an amino group and optionally conversion of such an amino group into a mono- or di-alkylamino group;

elimination of protecting groups on an amino group; conversion of a carboxy group to an alkoxycarbonyl group;

conversion of a single bond represented by the dotted line to a double bond;

acylation of appropriate heterocycles; salification.

Hydrolysis of an ester may be carried out by conventional means. For example, a suitable reaction comprises treating the compound of formula (Ia) with an alkali metal hydroxide (such as sodium hydroxide or potassium hydroxide) in an inert solvent (such as aqueous ethanol) at a suitable temperature, e.g. from 0° C. to 100° C., for a period of from 10 minutes to 2 hours.

Conversion of an alkoxycarbonyl group, an aryloxycarbonyl group, an aralkyloxycarbonyl group or a carboxy group to an optionally substituted hydrazinocarbonyl group or carbamoyl group may be carried out by reacting the compound of formula (Ia) (before or after one or more other optional reactions of step A2) with an amine derivative of formula (VI):

$$H-(NH)_n-NR^6R^7 \qquad (VI)$$

(in which n, $R^6$ and $R^7$ are as defined above) in an inert solvent.

The nature of the solvent employed is not critical to the reaction, provided that it has no adverse effect on the reaction. Suitable solvents include those exemplified in relation to step A1 above, as well as alcohols, such as methanol or ethanol. The reaction will take place over a wide temperature range, but we normally prefer to carry it out at a temperature within the range from 0° to 150° C. The time required for the reaction will vary depending upon many factors, particularly the reaction temperature and the nature of the reagents, but a period of from 30 minutes to 24 hours will normally suffice.

Conversion of a carboxylic acid into an amide may be carried out by reacting the corresponding compound of formula (Ia) (before or after one or more of the other optional reactions of step A2) with a compound of formula (VI), defined above, in the presence of a dehydrating agent and of an inert solvent. Suitable dehydrating agents include, for example: carbodiimides, such as dicyclohexylcarbodiimide; and cyanophosphoric acid esters, such as diethyl cyanophosphonate or dimethyl cyanophosphonate; of these, the cyanophosphoric acid esters are preferred. Suitable solvents include those illustrated in relation to step A1.

This reaction is preferably effected in the presence of a base, more preferably an organic amine, such as triethylamine, pyridine or 4-dimethylaminopyridine. The reaction will take place over a wide temperature range, but we generally prefer a temperature within the range from 0° to 50° C. The time required for the reaction will vary, depending upon many factors, notably the reaction temperature and the nature of the reagents, but a period of from 2 to 24 hours will normally suffice.

Alternatively, the same reaction may be effected by first converting the carboxylic acid into a reactive derivative thereof and then reacting this reactive derivative with the amine compound of formula (VI).

Suitable reactive derivatives of the carboxylic acid include: acid halides, such as the acid chloride; mixed acid anhydrides of the carboxylic acid with another organic carboxylic acid, such as acetic acid, propionic acid or pivalic acid; and active esters of the carboxylic acid, such as the isobutoxycarbonyl ester. These reactive derivatives can be prepared by treating the corresponding carboxylic acid with a suitable halogen compound, such as thionyl chloride, acetyl chloride, pivaloyl chloride or isobutoxycarbonyl chloride.

Where a reactive derivative of the carboxylic acid is employed, the reaction between the reactive derivative and the amine of formula (VI) is preferably effected in the presence of an inert solvent, the nature of which is not critical, provided that it has no adverse effect upon the reaction. Suitable solvents for this reaction include: hydrocarbons, which may be aliphatic, cycloaliphatic or aromatic, particularly benzene or hexane; and ethers, such as diethyl ether or tetrahydrofuran. Although the reaction can be carried out over a wide range of temperatures, we generally find it most convenient to effect the reaction at about ambient temperature. At such a temperature, the time required for the reaction will normally be within the range from 30 minutes to 3 hours.

Conversion of a nitro group into an amino group may be carried out by treating the compound of formula (Ia) (before or after one or more other optional reactions of step A2) with a reducing agent or by catalytic hydrogenation.

Suitable reducing agents include: a combination of an organic carboxylic acid (such as acetic acid or propionic acid) with a metal (such as zinc, iron, nickel or tin); and combinations of stannous chloride with a dilute mineral acid (such as dilute hydrochloric acid or dilute sulfuric acid). Of these, we prefer zinc/acetic acid or stannous chloride/dilute hydrochloric acid. This reaction is preferably effected in the presence of a solvent, the nature of which is not critical, provided that it has no adverse effect upon (although it may participate in) the reaction. Suitable solvents include: water; alcohols, such as methanol or ethanol; aqueous alcohols, such as aqueous methanol or aqueous ethanol; organic carboxylic acids, such as those mentioned above as part of the reducing agent system; and aqueous organic carboxylic acids, again such as those forming part of the reducing agent system.

In the case of catalytic hydrogenation, preferred catalysts include, for example, platinum oxide, palladium black, palladium-on-activated carbon and Raney nickel. Palladium-on-activated carbon is preferably used. The reaction is preferably effected under a hydrogen atmosphere, for example at a hydrogen pressure of from 1 to 10 atmospheres (about 1 to 10 bars). The reaction is preferably effected in the presence of a solvent, the nature of which is not critical, provided that it has no adverse effect on the reaction. Suitable solvents include, for example: alcohols, such as methanol or ethanol; ethers, such as tetrahydrofuran or dioxane; organic carboxylic acids, such as acetic acid or propionic acid; and mixtures of one or more of these organic solvents with water.

The reaction will take place over a wide range of temperatures, but we generally fine it convenient to carry out the reaction at a temperature within the range from 0° to 50° C. The time required for the reaction will vary, depending upon many factors, notably the reaction temperature and the nature of the reagents, but a period of from 30 minutes to 2 hours will normally suffice.

Conversion of a free amino group into a mono- or di-alkylamino group may be effected by reacting the corresponding amino compound with an alkyl halide (preferably a chloride, bromide or iodide), the nature of the alkyl group depending upon which alkyl group it is desired to introduce. The reaction is preferably effected in the presence of a base. Examples of suitable bases which may be employed include carbonates and bicarbonates, such as sodium carbonate, potassium carbonate, sodium bicarbonate or potassium bicarbonate. The reaction is preferably effected in the presence of an inert solvent, the nature of which is not critical, provided that it has no adverse effect upon the reaction. Suitable solvents include, for example: amides, such as dimethylformamide or dimethylacetamide; sulfoxides, such as dimethyl sulfoxide; alcohols, such as methanol or ethanol; water; and mixtures of one or more of these organic solvents with water.

The reaction will take place over a wide range of temperatures, but we generally find it convenient to carry out the reaction at a temperature of from 0° C. to 100° C. The time required for the reaction will vary, depending upon many factors, but a period of from 30 minutes to 5 hours will normally suffice.

In this reaction, the product will normally be a mixture of the monoalkylamino compound and the dialkylamino compound; use of approximately equimolar amounts of the alkyl halide and of the amino compound will result in the predominant production of the monoalkylamino compound; on the other hand, use of an excess of the alkyl halide will normally favour predominant production of the dialkylamino compound.

Elimination of a protecting group from the amin group may be effected by catalytic hydrogenation, details of the reaction being similar to those discussed above in relation to the catalytic hydrogenation of a nitro group into an amino group.

Conversion of a carboxy group to an alkoxycarbonyl group is a conventional esterification reaction. It may, for example, be carried out by reacting the corresponding carboxy compound with a diazoalkane corresponding to the alkoxy group of the alkoxycarbonyl group which it is desired to prepare, for example diazomethane, diazoethane or diazopropane. The reaction is preferably effected in the presence of an inert solvent, the nature of which is not critical, provided that it has no adverse effect on the reaction; suitable solvents include ethers, such as diethyl ether. The reaction temperature is likewise not critical, and we generally find it convenient to carry out the reaction at about ambient temperature.

Alternatively, this esterification may be carried out by reacting the corresponding carboxy compound with an alkanol, such as methanol, ethanol or butanol, in the presence of a dehydrating agent. Reagents and reaction conditions to be employed in this reaction are similar to those discussed above in relation to the reaction of a carboxylic acid with an amine.

Where the resulting compound of formula (Ia) (before or after any of the other optional reactions of step A2) has a single bond between the 4- and 5-positions of the pyridazinone system, this may be converted to the corresponding compound having a double bond in that position by one of two processes. One process comprises halogenating the single bond compound and then dehydrohalogenating the resulting halogenated compound. These two reactions may be carried out simultaneously in the same reaction medium, for example by treating the starting material with a halogen or with a suitable halogen compound (particularly chlorine or bromine) at a temperature of from 50° to 150° C. for a period of from 5 minutes to 1 hour in a carboxylic acid, such as acetic acid or propionic acid.

Alternatively, the single bond compound may be converted to the corresponding double bond compound by reaction with an alkali metal salt of a sulfonic acid (which may be an arylsulfonic acid) such as sodium m-nitrobenzenesulfonate, potassium m-nitrobenzenesulfonate or sodium 5-nitronaphthalene-1-sulfonate, in an aqueous alkali solution at a temperature of from 50° C. to 150° C. for a period of from 30 minutes to 5 hours.

Where the group represented by $R^3$ in the compound of formula (I) or (Ia) is or contains a heterocyclic ring containing at least one unsubstituted nitrogen atom, for example a piperazine or homopiperazine ring, this may, if desired, be acylated. The reaction is carried out by reacting the starting material with a reactive derivative of the carboxylic, sulfonic or other acid whose acyl group it is desired to introduce. In particular, such acylation may, for example, introduce an aliphatic, aromatic, cycloaliphatic, araliphatic or heterocyclic carboxylic acyl group, an aliphatic or aromatic sulfonyl group, an alkoxycarbonyl group, an aryloxycarbonyl group or an aralkyloxycarbonyl group.

The preferred reactive derivatives include the carboxylic acid anhydrides, carboxylic acid halides, sulfonic acid halides and halocarbonates. Preferred anhydrides are acetic anhydride, propionic anhydride, butyric anhydride, valeric anhydride, octanoic anhydride and optionally substituted benzoic anhydride. Preferred halides are chlorides and bromides, e.g. acetyl chloride, propionyl chloride, butyryl chloride, valeryl chloride, octanoyl chloride, acryloyl chloride, crotonoyl chloride, optionally substituted benzoyl chloride, optionally substituted benzoyl bromide, nicotinoyl chloride, furoyl chloride, thenoyl chloride, methanesulfonyl chloride, ethanesulfonyl chloride, hexanesulfonyl chloride, optionally substituted benzenesulfonyl chloride, methyl chlorocarbonate, ethyl chlorocarbonate, hexyl chlorocarbonate, phenyl chlorocarbonate and benzyl chlorocarbonate. The reaction is preferably effected in the presence of an inert solvent and of a base. The nature of the solvent employed is not critical, provided that it has no adverse effect upon the reaction. Examples of suitable solvents include: hydrocarbons, such as hexane, cyclohexane, benzene, toluene or xylene; ethers such as diethyl ether, tetrahydrofuran or dioxane; and halogenated hydrocarbons such as methylene chloride, chloroform or carbon tetrachloride. Where the reactive derivtive is an acid anhydride, we prefer to use an excess of the base as the reaction solvent. Preferred bases are organic amines, for example pyridine, N,N-dimethylaniline or triethylamine, more preferably pyridine.

The reaction will take place over a wide range of temperatures, but we generally find it convenient to carry out this reaction at about ambient temperature. The time required for the reaction will vary, depending upon many factors, notably the nature of the reagents and the reaction temperature, but a period of from 1 hour to 1 day will normally suffice.

At the end of any of these reactions, the desired compound may be recovered from the reaction mixture by conventional means. For example, one suitable recovery procedure comprises: pouring the reaction mixture either directly or after distilling off the solvent into ice-water; if necessary, neutralising the resulting mixture; extracting the mixture with a water-immiscible organic solvent; washing with water and then drying the extract; and finally distilling the solvent from the extract to give the desired product. If necessary, this may be further purified by conventional means, for example recrystallization or the various chromatography techniques, particularly column chromatography.

Method B

In this Method, the compounds of the invention are prepared by reacting a phenyl derivative with succinic or maleic anhydride, or a derivative thereof, and then reacting the product with hydrazine, as illustrated in the following reaction scheme:

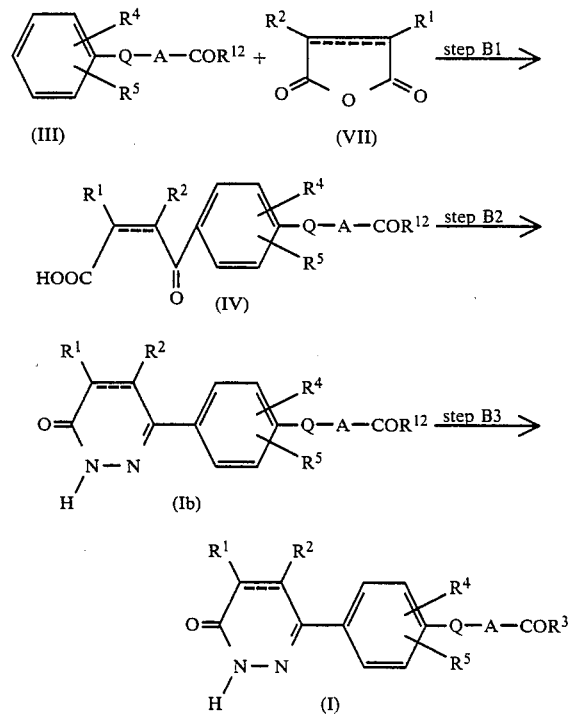

In the above formulae, $R^1$, $R^2$, $R^3$, $R^4$, $R^5$, $R^{12}$, Q, A and the dotted line are as defined above.

Step B1 of this Method comprises reacting the phenyl derivative of formula (III) with the succinic or maleic anhydride or derivative thereof of formula (VII). The reaction is preferably effected in the presence of an acid catalyst and in an inert solvent.

The nature of the acid catalyst employed is not critical and any acid catalyst commonly used in Friedel-Crafts reactions may be employed. Examples of such acid catalysts include: Lewis acids, such as aluminum chloride, zinc chloride, ferric chloride, titanium tetrachloride or boron trifluoride; and protonic acids, such as hydrofluoric acid or sulfuric acid. Of these, aluminum chloride is preferred.

There is no particular limitation on the nature of the inert solvent to be employed in this reaction, provided that it does not interfere with the reaction. Examples of suitable solvents include: halogenated hydrocarbons, preferably halogenated aliphatic hydrocarbons, such as methylene chloride, chloroform or carbon tetrachloride; and amides, such as dimethylformamide and dimethylacetamide. Of these, methylene chloride is preferred.

The reaction will take place over a wide range of temperatures, but we normally find it convenient to carry out the reaction at a temperature of from 0° to 50° C. The time required for the reaction will vary, depending upon many factors, notably the reaction temperature and the nature of the reagents, but a period of from 1 hour to 5 hours will normally suffice.

After completion of this reaction, the resulting compound of formula (IV) may be recovered from the reaction mixture by conventional means. For example, one suitable recovery technique comprises: pouring the reaction mixture into ice-water; extracting the mixture with a water-immiscible organic solvent; washing the extract with water and then drying it; and finally distilling the solvent from the extract to give the required compound. If desired, this compound may be further purified by conventional methods, for example recrystallization or the various chromatography techniques, particularly column chromatography.

In step B2 of this method, the compound of formula (IV), obtained in step B1, is reacted with hydrazine in an inert solvent, to give the compound of formula (Ib).

The nature of the solvent employed in this process is not critical, provided that it has no adverse effect upon the reaction. Examples of suitable solvents include: alcohols, such as methanol, ethanol and propanol; ethers, such as diethyl ether or tetrahydrofuran; water; and mixtures of one or more of the above organic solvents with water. Of these, we prefer the alcohols.

The reaction will take place over a wide range of temperatures, but we generally find it convenient to carry out the reaction at a temperature of from 0° to 100° C. The time required for the reaction will vary, depending upon many factors, notably the reaction temperature and the nature of the reagents, but a period of from 2 to 10 hours will normally suffice.

After completion of the reaction, the desired compound of formula (Ib) may be recovered from the reaction mixture by conventional means. For example, one suitable recovery procedure comprises: pouring the reaction mixture into ice-water, optionally after distilling off the solvent; extracting the mixture with a water-immiscible organic solvent; washing the extract with water and drying it; and finally distilling the solvent from the extract. If necessary, this product may be further purified by such conventional techniques as recrystallization or the various chromatography techniques, particular column chromatography.

If the carbonyl group attached to the group represented by $R^3$ or any carbonyl group within the groups represented by $R^4$ or $R^5$ is converted by this reaction into a hydrazone group ($>C=N-NH_2$), the carbonyl group may be regenerated by treating the resulting compound with an acid in an inert solvent. Suitable acids include: organic carboxylic acids, such as acetic acid or propionic acid; and dilute mineral acids, such as dilute hydrochloric acid or dilute sulfuric acid. The nature of the solvent employed is not critical, provided that it does not interfere with the reaction. Suitable solvents include, for example: water; alcohols, such as methanol or ethanol; ethers, such as diethyl ether or dioxane; and mixtures of one or more of the above organic solvents with water.

The reaction will take place over a wide range of temperatures, but we generally find it convenient to employ a temperature within the range from 20° to 100° C. The time required for the reaction will vary, depending upon many factors, notably the reaction temperature and the nature of the reagents, but a period of from 10 minutes to 3 hours will normally suffice.

Step B3 includes the same reactions as described in relation to step A2 and may be carried out in the same way.

Biological Activity

The compounds of the present invention have been found to possess excellent myocardial contractivity, anti-hypertensive activity and other similar activities, which appear to be better than those of the known pyridazinone compounds. Accordingly, it is anticipated that the compounds of the invention will be of considerable therapeutic use as cardiac stimulants, anti-hypertensive drugs and anti-thrombotic agents.

The cardiac activity of the compounds of the invention is illustrated by the following tests.

Cardiac Activity in the Dog Heart

Following the method reported by Alousi et al [Circulation Research 45, 666 (1979)], a fine catheter, having a pressure sensor built in at the top was inserted into the carotid artery of an anaesthetised dog in the direction of the heart. The top part of the catheter was placed in the left ventricle and the pressure waveform obtained was recorded by its linear differential value. The value for the contraction of the left ventricle was taken as the maximum value of this pressure wave.

Each test compound was dissolved either in 0.1N hydrochloric acid or in dimethylformamide and administered intravenously (Table 1) or intraduodenally (Table 2) and the percentage increase in contractive power from its level immediately prior to administration, as well as the recovery time (in minutes) are shown in the following Tables. The recovery time measured was the time taken, after administration of the test compound, for the heart contractive power to return to its level immediately prior to administration. For purposes of comparison, two prior art compounds were similarly tested. Compound A is 4,5-dihydro-6-(p-methoxyphenyl)-3(2H)-pyridazinone, one of the compounds disclosed in Japanese Patent Application Kokai No. 8015/83; Compound B is amrinone, whose systematic name is 5-amino-(3,4'-bipyridin)-6(1H)-one, which is currently used as a cardiotonic.

TABLE 1

| Cpd No. | Dosage (mg/kg) | Contractive power (% increase) | Recovery time (minutes) |
| --- | --- | --- | --- |
| 63a | 0.010 | 54 | 31 |
| 96b | 0.003 | 52 | 38 |
| 105a | 0.010 | 83 | 67 |
| 109a | 0.010 | 42 | 76 |
| 116a | 0.003 | 43 | 107 |
| 127a | 0.010 | 71 | 46 |
| 167a | 0.010 | 59 | 56 |
| 168a | 0.010 | 61 | 135 |
| 206a | 0.003 | 32 | 74 |
| Cpd. A | 0.010 | 18 | 15 |
| Cpd. B | 0.300 | 21 | 27 |

TABLE 2

| Cpd. No. | Dosage (mg/kg) | Contractive power (% increase) |
| --- | --- | --- |
| 105a | 0.1 | 77 |
| 127a | 0.1 | 85 |

As can be seen from the above results, particularly those in Table 1, the compounds of the invention potentiated the contractions of the heart significantly better than the two known compounds, including amrinone, which is sold commercially for this specific purpose; moreover, the effect of the compounds of the invention was more durable. As can be seen from Table 2, the compounds of the invention significantly potentiate the contractions of the heart when administered intraduodenally at doses not greater than 10 times the optimal intravenous dose; moreover, the compounds are well absorbed in the digestive tract.

The compounds of the invention can be administered as conventional pharmaceutical formulations, depending upon the intended route of administration. For example, for oral administration, they may be formulated as powders, granules, tablets, capsules or similar orally administerable formulations, which can be produced by mixing the active compound with carriers, excipients or diluting agents, such as glucose, sucrose, lactose, sorbitol, starch, polyvinylpyrrolidone, mannitol, calcium carbonate, calcium phosphate, sodium chloride or boric acid. For parenteral administration, they may be formulated as conventional injections suitable for, for example, intravenous injection. The dose will vary, depending upon the nature of the disorder, the route of administration, and the symptoms, age and body weight of the patient; however, for an adult human patient, a suitable dose would be from 0.001 mg to 50 mg per day, which could be given in a single dose or in divided doses.

The invention is further illustrated by the following Examples, which illustrate the preparation of various of the compounds of the invention. The preparation of certain of the starting materials employed in these Examples is illustrated in the subsequent Preparations.

EXAMPLE 1

6-[3-Chloro-4-(ethoxycarbonylmethoxy)phenyl]-4,5-dihydro-3(2H)-pyridazinone (Compound No. 6a)

1.79 g of 6-(3-chloro-4-hydroxyphenyl)-4,5-dihydro-3(2H)-pyridazinone (prepared as in Preparation 8) was dissolved in 15 ml of anhydrous dimethylformamide. 0.35 g of a 55% w/w suspension of sodium hydride in mineral oil was added, and the solution was stirred for 1 hour. To this solution, was added, whilst ice-cooling, 1 ml of a dimethylformamide solution containing 1.34 g of ethyl bromoacetate, and the mixture was stirred for 1 hour at room temperature and then for 3 hours at 80° C. At the end of this time, the dimethylforamide was distilled off under reduced pressure and the mixture was diluted with water and then extracted with ethyl acetate. The extract was washed with water, dried and then evaporated to dryness. The addition of hexane precipitated 1.85 g of the title compound as white needles melting at 134°–136° C.

Elemental Analysis: Calculated for $C_{14}H_{15}N_2O_4Cl$: C, 54.11%; H, 4.87%; N, 9.01%; Cl, 11.41%. Found: C, 54.16%; H, 4.87%; N, 8.63%; Cl, 11.23%.

EXAMPLE 2

6-[3-Chloro-4-carboxymethoxy)phenyl]-4,5-dihydro-3(2H)-pyridazinone (Compound No. 1a)

50 ml of a 50% v/v aqueous ethanol solution containing 5 g of 6-[3-chloro-4-(ethoxycarbonylmethoxy)-phenyl]-4,5-dihydro-3(2H)-pyridazinone (Compound No. 6a, prepared as described in Example 1) and 2.5 g of sodium hydroxide were stirred together for 40 minutes at 80° C. and then cooled. The solution was acidified with hydrochloric acid and the crystals which precipitated were recrystallized from aqueous ethanol, to give 3.35 g (yield 73.79%) of the title compound as white crystals, melting at 214°–216° C.

Elemental Analysis: Calculated for $C_{12}H_{11}N_2O_4Cl$: C, 50.99%, H, 3.92%; N, 9.91%; Cl, 12.54%. Found: C, 51.29%; H, 3.92%; N, 9.71%; Cl, 12.45%.

EXAMPLE 3

6-{3-Chloro-4-[N-(2-morpholinoethyl)carbamoylmethoxy]phenyl}-4,5-dihydro-3(2H)-pyridazinone (Compound No. 167a)

0.7 g of 6-[3-chloro-4-(carboxymethoxy)phenyl]-4,5-dihydro-3(2H)-pyridazinone (Compound No. 1a, prepared as described in Example 2) and 0.35 g of N-(2-aminoethyl)morpholine were dissolved in 8 ml of dimethylformamide. To this solution were added 0.55 g of trimethylamine and 0.5 g of 90% diethyl cyanophosphonate, whilst ice cooling. The reaction mixture was then allowed to stand for one day and overnight at ambient temperature, after which it was poured into ice-water. The crystals which precipitated were collected by filtration. Recrystallization from ethanol gave 0.6 g (yield 61.2%) of the title compound as white crystals melting at 193°–194° C.

Elemental Analysis: Calculated for $C_{18}H_{23}N_4O_4Cl$: C, 54.75%; H, 5.87%; N, 14.19%; Cl, 8.92%. Found: C, 54.59%; H, 5.97%; N, 14.29%; Cl, 8.72%.

EXAMPLE 4

6-[3-Chloro-4-(N-butylcarbamoylmethoxy)phenyl]-4,5-dihydro-3(2H)-pyridazinone (Compound No. 43a)

6 ml of a dimethylformamide solution containing 0.8 g of 6-[3-chloro-4-(ethoxycarbonylmethoxy)phenyl]-4,5-dihydro-3(2H)-pyridazinone (Compound No. 6a, prepared as described in Example 1) and 4 ml of butylamine was stirred for 7 hours at 120° C. This solution was then poured into ice-water and the crystals which precipitated were collected by filtration. Recrystallization of these from dimethylformamide gave 0.6 g (yield 62.8%) of the title compound as white crystals melting at 140°–141° C.

Elemental Analysis: Calculated for $C_{16}H_{20}N_3O_3Cl$: C, 56.89%; H, 5.97%; N, 12.44%; Cl, 10.49%. Found: C, 56.80%; H, 6.08%; N, 12.34%; Cl, 10.56%.

EXAMPLE 5

6-{3-Chloro-4-[N-(2-morpholinoethyl)carbamoylmethoxy]phenyl}-3(2H)-pyridazinone (Compound No. 167b)

1.5 g of 6-{3-chloro-4-[N-(2-morpholinoethyl)carbamoylmethoxy]phenyl}-4,5-dihydro-3(2H)-pyridazinone (Compound No. 167a, prepared as described in Example 3) was dissolved in 18 ml of acetic acid, and 2 ml of acetic acid containing 0.65 g of bromine were then added dropwise at 100° C. to the resulting solution. After completion of the addition, the reaction mixture was stirred for 10 minutes at the same temperature and then poured into ice-water. This solution was neutralized with sodium carbonate and then extracted with ethyl acetate. The extract was dried and then concentrated by evaporation under reduced pressure. The residue was purified by silica gel column chromatography (eluting solvent: ethyl acetate:ethanol=9:1 by volume). Recrystallization from ethanol gave 0.4 g (yield 27.01%) of the title compound as white needles melting at 201°–202° C.

EXAMPLE 6

6-[4-(N-Propylcarbamoylmethoxy)phenyl]-4,5-dihydro-3(2H)-pyridazinone (Compound No. 32a)

6(a)

4-[p-(N-Propylcarbamoylmethoxy)phenyl]-4-oxobutyric acid 1.54 g of N-propyl-α-phenoxyacetamide and 0.8 g of succinic anhydride were dissolved in 20 ml of methylene chloride. 3.36 g of aluminum chloride were added slowly to the solution, whilst holding the temperature at −5° C. to 0° C. When the addition was complete, the reaction mixture was stirred for 2 hours at room temperature and then poured into ice-water acidified with hydrochloric acid. The solution was then extracted with ethyl acetate, and the extract was washed with water, dried and evaporated to dryness, to obtain crystals. Recrystallization of these from a mixture of methanol and ethyl acetate gave 0.6 g of the title compound as white crystals melting at 122°–124° C.

Elemental Analysis: Calculated for $C_{15}H_{19}NO_5$: C, 61.21%; H, 6.85%; N, 4.76%. Found: C, 61.46%; H, 6.93%; N, 4.88%.

6(b)

6-[4-(N-Propylcarbamoylmethoxy)phenyl]-4,5-dihydro-3(2H)-pyridazinone (Compound No. 32a)

2.35 g of 4-[p-(N-propylcarbamoylmethoxy)phenyl]-4-oxobutyric acid [prepared as described in step (a) above] and 0.33 g of 80% hydrazine were dissolved in 40 ml of methanol. This solution was heated under reflux and then concentrated by evaporation under reduced pressure. The residue was cooled to obtain 1.6 g of the title compound as white crystals melting at 162°–165° C.

Elemental Analysis: Calculated for $C_{15}H_{19}N_3O_3$: C, 62.27%; H, 6.62%; N, 14.52%. Found: C, 62.19%; H, 6.64%; N, 14.58%.

EXAMPLE 7

6-{3-Chloro-4-[N'-(3-phenylpropionyl)hydrazinocarbonylmethoxy]}-4,5-dihydro-3(2H)-pyridazinone (Compound No. 157a)

0.89 g of 6-[3-chloro-4-(hydrazinocarbonylmethoxy)phenyl]-4,5-dihydro-3(2H)-pyridazinone (Compound No. 18a, prepared following the procedure described in Example 4) was dissolved in 20 ml of pyridine, and 0.51 g of β-phenylpropionyl chloride was added thereto at room temperature, with stirring. The mixture was then stirred at the same temperature for 3 hours, after which the solvent was distilled off in vacuo and water was added to the resulting residue. The resulting precipitate was filtered off, washed with water, dried and recrystallized from methanol, to give 1.2 g of the title compound melting at 222°–223° C.

EXAMPLE 8

6-[3-Chloro-4-(4-methoxybenzylideneaminocarbamoylmethoxy)phenyl]-4,5-dihydro-3(2H)-pyridazinone (Compound No. 160a)

1.00 g of 6-[3-chloro-4-(hydrazinocarbonylmethoxy)phenyl]-4,5-dihydro-3(2H)-pyridazinone (Compound No. 18a, prepared following the procedure described in Example 4) was dissolved in 55 ml of dimethylformamide, and 2.3 g of p-anisaldehyde were added, at room temperature, to the resulting solution. The mixture was then stirred at the same temperature for 8 hours. At the end of this time, the solvent was distilled off in vacuo and chloroform was added to the resulting residue. The resulting precipitate was filtered off to give 1.28 g of the title compound melting at 220°–222° C.

EXAMPLE 9

6-[3-Chloro-4-(allylcarbamoylmethoxy)phenyl]-4,5-dihydro-3(2H)-pyridazinone (Compound No. 135a)

Following the same procedure as described in Example 3, the title compound, melting at 145°–146° C., was prepared from 6-[3-chloro-4-(carboxymethoxy)phenyl]-4,5-dihydro-3(2H)-pyridazinone (Compound No. 1a, prepared as described in Example 2) and allylamine.

EXAMPLE 10

6-[3-Chloro-4-(ethoxycarbonylmethoxy)phenyl]-4,5-dihydro-3(2H)-pyridazinone (Compound No. 6a)

10(a)

4-[3-Chloro-4-(ethoxycarbonylmethoxy)phenyl]-4-oxobutyric acid 12.9 g of ethyl 2-chlorophenoxyacetate (prepared as described in Preparation 1) and 6.00 g of succinic anhydride were dissolved in 70 ml of methylene chloride, and 25.2 g of aluminum trichloride were added thereto in small portions at 0°–5° C., with stirring. The mixture was then stirred at room temperature for 3 hours, poured into ice-water and then extracted with ethyl acetate. The extract was washed with water and dried. The solvent was distilled off in vacuo and the resulting precipitate was recrystallized from a mixture of ethyl acetate and hexane, to give 14.3 g of the title compound melting at 137°–139° C.

10(b)

6-[3-Chloro-4-(ethoxycarbonylmethoxy)phenyl]-4,5-dihydro-3(2H)-pyridazinone (Compound No. 6a)

1.58 g of 4-[3-chloro-4-(ethoxycarbonylmethoxy)-phenyl]-4-oxobutyric acid [prepared as described in step (a) above] was dissolved in 10 ml of ethanol and 0.31 g of 80% v/v aqueous hydrazine hydrate was added thereto, whilst ice-cooling. The mixture was stirred, with ice-cooling, for 5 minutes, and then heated under reflux for 3 hours, after which ethyl acetate was added thereto. The mixture was then cooled to room temperature and the resulting precipitate was recrystallized from a mixture of ethyl acetate and hexane, to give 1.49 g of the title compound, having the same characteristics as the product of Example 1.

EXAMPLE 11

6-[3-Chloro-4-(carboxymethoxy)phenyl]-3(2H)-pyridazinone (Compound No. 1b)

1.91 g of 6-[3-chloro-4-(carboxymethoxy)phenyl]-4,5-dihydro-3(2H)-pyridazinone (Compound No. 1a, prepared as described in Example 2) was dissolved in 55 ml of a 2% w/v aqueous sodium hydroxide solution, and 1.6 g of sodium m-nitrobenzenesulfonate was added thereto. The mixture was heated, with stirring, over an oil bath at 120° C. for 2 hours. The mixture was then cooled to room temperature and then acidified with 6N hydrochloric acid to a pH value of 2-3. The resulting precipitate was collected by filtration, to give 1.2 g of the title compound, melting at 227°=232° C.

EXAMPLE 12

6-{3-Chloro-4-[N-(2-morpholinoethyl)carbamoylmethoxy]phenyl}-3(2H)-pyridazinone (Compound No. 167b)

Following the same procedure as described in Example 3, the title compound, melting at 201°-212° C., was prepared from 6-[3-chloro-4-(carboxymethoxy)phenyl]-3(2H)pyridazinone (Compound No. 1b, prepared as described in Example 11) and N-(2-aminoethyl)morpholine.

EXAMPLE 13

6-{3-Chloro-4-[N-(2-piperazin-1-ylethyl)carbamoylmethoxy]phenyl}-4,5-dihydro-3(2H)-pyridazinone (Compound No. 220a)

5.0 g of 6-[3-chloro-4-(ethoxycarbonylmethoxy)-phenyl]-4,5-dihydro-3(2H)-pyridazinone (Compound No. 6a, prepared as described in Example 1) and 2.18 g of N-(2-aminoethyl)piperazine were mixed, and the mixture was heated, with stirring, over an oil bath at 130°-140° C. for 50 minutes. The mixture was cooled to room temperature, and then ethanol was added thereto and an insoluble material was filtered off. The filtrate was concentrated by evaporation in vacuo and the residue was crystallized by the addition of isopropyl alcohol. The resulting crystals were collected by filtration to give 3.9 g of the crude title compound, which was further purified by recrystallization from ethanol to give the pure compound, melting at 176°-178° C.

EXAMPLE 14

6-[3-Chloro-4-{N-[2-(4-acetylpiperazin-1-yl)ethyl]carbamoylmethoxy}phenyl]-4,5-dihydro-3(2H)-pyridazinone (Compound No. 236a)

0.5 g of 6-{3-chloro-4-[N-(2-piperazin-1-ylethyl)carbamoylmethoxy]phenyl}-4,5-dihydro-3(2H)-pyridazinone (Compound No. 220a, prepared as described in Example 13) was suspended in 6 ml of pyridine, and 0.29 g of acetic anhydride was added thereto at room temperature, with stirring. The mixture was then stirred at the same temperature for 1.5 hours and allowed to stand overnight. The solvent was then distilled off in vacuo and the residue was purified by silica gel column chromatography, eluted with 5% v/v ethanol in methylene chloride, followed by recrystallization from isopropyl alcohol to yield 0.36 g of the title compound, melting at 183°-185° C.

EXAMPLE 15

6-{3-Chloro-4-[N-(2,5-dimethyl-1-pyrrolyl)carbamoylmethoxy]phenyl}-4,5-dihydro-3(2H)-pyridazinone (Compound No. 143a)

0.50 g of 6-[3-chloro-4-(hydrazinocarbonylmethoxy)-phenyl]-4,5-dihydro-3(2H)-pyridazinone (Compound No. 18a, prepared as described in Example 4) was dissolved in 3 ml of acetic acid, and 0.23 g of acetonylacetone was added dropwise thereto, with stirring. The mixture ws then stirred at 70° C. for 3 hours, after which it was cooled to room temperature. The solvent was then distilled off under reduced pressure and the resulting residue was dissolved in ethyl acetate. This solution was washed with a 5% v/v aqueous sodium bicarbonate solution and then with water, and dried. The solvent was distilled off under reduced pressure and the resulting residue was purified by silica gel column chromatography; eluted with 5% v/v triethylamine in ethyl acetate, to yield 0.43 of the title compound melting at 188°-190° C.

The following compounds were also prepared by the appropriate one of the procedures described in the preceding Examples. The compounds are identified by the numbers heretofore assigned to them.

| Cpd No | melting at (°C.) | prepared as in Example No |
| --- | --- | --- |
| 3a | 126-128 | 1 |
| 4a | 115-117 | 1 |
| 5a | 85-87 | 1 |
| 7a | 155-157 | 1 |
| 8a | 137-139 | 1 |
| 9a | 120-121 | 1 |
| 10a | 142-145 | 1 |
| 11a | 154-155 | 1 |
| 12a | 198-200 | 1 |
| 13a | 126-128 | 1 |
| 14a | 99-101 | 1 |
| 15a | 169-170 | 1 |
| 16a | 240-242 | 4(*) |
| 18a | 217-219 | 4 |
| 19a | 215-219 | 4(*) |
| 20a | 166-168 | 4(*) |
| 21a | 203-205 | 4(*) |
| 23a | 238-239 | 4(*) |
| 24a | 160-162 | 4(*) |
| 26a | 178-179 | 4(*) |
| 27a | 168-169 | 4(*) |
| 30a | 173-175 | 3 |
| 32a | 162-165 | 4(*) |
| 33a | 137-139 | 4 |
| 34a | 151-153 | 4(*) |

| Cpd No | melting at (°C.) | prepared as in Example No |
|---|---|---|
| 37a | 156–157 | 4(*) |
| 38a | 129–130 | 4(*) |
| 39a | 137–139 | 3 |
| 40a | 176–178 | 3 |
| 42a | 150–153 | 4(*) |
| 44a | 121–124 | 4 |
| 45a | 127–129 | 3 |
| 46a | 146–149 | 3 |
| 47a | 152–154 | 4 |
| 49a | 155–156 | 4 |
| 51a | 134–135 | 4 |
| 52a | 130–132 | 4(*****) |
| 54a | 126–127 | 4(*****) |
| 56a | 129–130 | 4(*****) |
| 59a | 155–157 | 3 |
| 63a | 164–166 | 4(*) |
| 67a | 95–97 | 4(*) |
| 69a | 185–187 | 4 |
| 75a | oil(**) | 4 |
| 76a | oil(***) | 4 |
| 79a | 188–190 | 3 |
| 80a | 126–128 | 3 |
| 85a | 172–175 | 3 |
| 87a | 170–172 | 3 |
| 88a | 154 (dec.) | 3 |
| 90a | 112–115 | 3 |
| 91a | 165–167 | 3 |
| 92a | 117–119 | 4(*****) |
| 96a | 197–199 | 3 |
| 96b | 210–212 | 5 |
| 104a | 144–145 | 3 |
| 105a | 186–188 | 3 |
| 106a | 132–135 | 3 |
| 107a | 130–132 | 3 |
| 108a | 177–178 | 4 |
| 109a | 160–162 | 4(*****) |
| 111a | 185–186 | 3 |
| 113a | 161–163 | 3 |
| 116a | 118–120 | 4(*****) |
| 120a | 159–160 | 3 |
| 122a | 148–150 | 3 |
| 124a | 199–201 | 4 |
| 125a | 174–176 | 3 |
| 126a | 150–151 | 3 |
| 127a | 150–152 | 3 |
| 128a | 163–164 | 3 |
| 129a | 143–145 | 3 |
| 130a | 170–172 | 3 |
| 133a | 218–219 | 3 |
| 134a | 174–176 | 3 |
| 138a | 167–169 | 3 |
| 139a | 196–198 | 3 |
| 140a | 198–200 | 3 |
| 145a | 197–198 | 3 |
| 147a | 119–121(****) | 3 |
| 148a | 215–216 | 3 |
| 149a | 220–221 | 3 |
| 150a | 252–253 (dec) | 3 |
| 151a | 189–190 | 3 |
| 152a | 142–143 | 3 |
| 154a | 204–205 | 7 |
| 156a | 143–145 | 7 |
| 158a | 264–265 | 7 |
| 167a | 234 (as hydrochloride) | 4(*****) |
| 168a | 160–162 | 3 |
| 168a | 217–218 (as hydrochloride) | 4(*****) |
| 168b | 125–129 | 5 |
| 169a | 156–157 | 3 |
| 170a | 136–137 | 4 |
| 171a | 193–194 | 3 |
| 172a | 167–170 | 4(*****) |
| 174a | 202–204 | 3 |
| 175a | 169–170 | 3 |
| 181a | 155–159 | 3 |
| 183a | 75 (dec.) | 3 |
| 184a | 148–150 | 4 |
| 185a | 67–70 | 4 |
| 193a | 164–167 | 4 |
| 194a | 54–56 (dec.) | 4(*) |
| 195a | 62–63 (dec.) | 4(*) |
| 197a | 155–157 | 3 |
| 198a | 68–70 (dec.) | 4(*) |
| 199a | 68–70 (dec.) | 4(*) |
| 201a | 232–234 | 4(*****) |
| 202a | 159–160 | 4(*****) |
| 206a | 160–162 | 4(*****) |
| 208a | 225–226 | 3 |
| 224a | 198–200 | 4(*****) |
| 226a | 230–231 | 3 |
| 241a | 152–153 | 14(******) |
| 243a | 202–204 | 14(******) |
| 246a | 170–171 | 14(******) |
| 250a | 160–162 | 14(******) |
| 254a | 242–246 | 3 |
| 271a | 197–198 | 3 |
| 272a | 157–158 | 3 |
| 306a | 156–158 | 14(******) |
| 307a | 79–81 | 14(******) |

(*)reacted in ethanol at 70° C. for 2 hours.
(**)Infrared Absorption Spectrum (CHCl$_3$) $v_{max}$cm$^{-1}$: 1675.
(***)Infrared Absorption Spectrum (CHCl$_3$) $v_{max}$cm$^{-1}$: 1680.
(****)as hydrochloride hydrate.
(*****)reacted without any solvent at 120° C. for 2 hours.
(******)corresponding acid chloride used.

PREPARATION 1

Ethyl 2-chlorophenoxyacetate

A mixture of 51.4 g of o-chlorophenol, 58.8 g of ethyl chloroacetate, 55.3 g of potassium carbonate and 250 ml of acetone was heated under reflux for 7 hours. The mixture was then cooled to room temperature and an insoluble material was filtered off. The filtrate was concentrated in vacuo and the resulting residue was purified by silica gel column chromatography to give 69.0 g of the title compound as an oil, boiling at 134°–137° C./2 mm Hg (267 Pa).

PREPARATION 2

6-(3-Methyl-4-hydroxyphenyl)-4,5-dihydroxy-3(2H)-pyridazinone (a) 4-(3-Methyl-4-hydroxyphenyl)-4-oxobutyric acid 24.5 g of O-methylanisole and 20.0 g of succinic anhydride were dissolved in 230 ml of methylene chloride. Holding the temperature of the reaction solution below 5° C., 84 g of aluminum chloride were slowly added. After the addition was complete, the reaction mixture was stirred for 1 hour at a temperature below 5° C. and for an additional 5 hours at room temperature. It was then allowed to stand for one day and overnight at room temperature, after which the reaction mixture was poured into ice-cooled dilute hydrochloric acid and the resulting precipitate was collected by filtration. The precipitate was washed and then dissolved in ethanol. This solution was dried by azeotropic distillation and then evaporated to dryness. 4.16 g of the title compound were obtained as an oil.

Infrared Absorption Spectrum (liquid film) $v_{max}$cm$^{-1}$: 1715, 1690.

(b) 6-(3-Methyl-4-hydroxyphenyl)-4,5-dihydroxy-3(2H)-pyridazinone 41.6 g of the compound prepared as described in step (a) were dissolved in 400 ml of ethanol. To this solution were slowly added, with ice-cooling, 8.2 g of 80% v/v aqueous hydrazine hydrate. After the addition was complete, the reaction mixture was stirred for 20 minutes and then heated under reflux, with stirring, for 3 hours. This reaction mixture was then allowed to stand for one day and overnight, after which it was cooled in ice-water. The resulting precipitate was collected by filtration and recrystallized from a mixture of ethanol and ethyl acetate, to give 22.7 g of the title compound melting at 265°–267° C.

Following the same procedure as described above, the pyridazinone derivatives of formula (IIa) shown below were obtained:

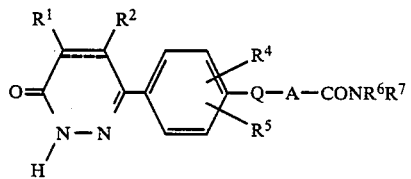

(IIa)

| Preparation No. | $R^1$ | $R^2$ | $R^4$ | $R^5$ | M.P. (°C.) |
|---|---|---|---|---|---|
| 3 | H | H | 2-Cl | 3-Cl | 210–220 |
| 4 | H | H | 2-Cl | H | 238–240 |
| 5 | H | H | 3-Me | H | 265–267 |
| 6 | H | Me | H | H | 254–256 |
| 7 | Me | H | 3-Cl | H | 205–207 |
| 8 | H | H | 3-Cl | H | 265–267 |

We claim:
1. A compound of formula (I):

$$\begin{array}{c}R^1\quad R^2\\O=\!\!\!\!\diagdown\!\!\!\!\diagup\!\!\!\!-\!\!\!\!\diagdown\!\!-\!\!\!\!\bigcirc\!\!-Q-A-CONR^6R^7\\N-N\\H\end{array}$$ (I)

$R^1$ and $R^2$ are independently selected from the group consisting of hydrogen atoms and methyl groups;
Q represents an oxygen atom;
A represents a $C_1$–$C_4$ alkylene group;
$R^6$ and $R^7$ are independently selected from the group consisting of hydrogen atoms; $C_1$–$C_6$ alkyl groups; $C_5$ and $C_6$ cycloalkyl groups; 2,5-dimethylpyrrolyl groups; $C_3$ and $C_4$ alkenyl groups; heterocyclic groups selected from the group consisting of: tetrahydrofuryl, tetrahydropyranyl, tetrahydrothiofuryl, tetrahydrothiopyranyl, pyrrolidinyl, piperidyl, imidazolidinyl, oxazolidinyl, thiazolidinyl, morpholinyl, thiomorpholinyl and piperazinyl groups;
said heterocyclic groups having at least one substituent selected from the group consisting of:
methyl, ethyl, phenyl, methoxycarbonyl, ethoxycarbonyl, benzyl, oxygen, hydroxyethyl, chlorophenyl, methoxyphenyl, trifluoromethylphenyl, pyridyl, benzhydryl, chlorobenzhydryl, difluorobenzhydryl, formyl, acetyl, valeryl, 3-butenoyl, chlorobutyryl, ethoxyacetyl, benzyloxycarbonyl, methanesulfonyl, toluenesulfonyl, benzoyl, chlorobenzoyl, methoxybenzoyl, nicotinoyl, isonicotinoyl, thenoyl, furoyl, methylcarbamoyl, p-chloro-m-sulfamoylbenzoyl, propionyl, isobutyryl, octanoyl, phenylpropionyl, cyclohexylpropionyl, heptanoyl and dimethoxybenzoyl groups;
and substituted $C_1$–$C_4$ alkyl groups having at least one substituent selected from the group consisting of:
$C_1$–$C_4$ alkoxy groups, $C_2$ and $C_3$ alkoxycarbonyl groups, morpholino groups, thiomorpholino groups, piperazinyl groups, homopiperazinyl groups, phenyl groups, phenyl groups having at least one substituent selected from the group consisting of halogen, $C_1$–$C_4$ alkyl, $C_1$–$C_4$ alkoxy and trifluoromethyl substituents, pyridyl groups and 1-piperazinyl groups having at the 4-position at least one substituent selected from the group consisting of methyl, ethyl, phenyl, methoxycarbonyl, ethoxycarbonyl, benzyl, oxygen, hydroxyethyl, chlorophenyl, methoxyphenyl, trifluoromethylphenyl, pyridyl, benzhydryl, chlorobenzhydryl, difluorobenzhydryl, formyl, acetyl, valeryl, 3-butenoyl, chlorobutyryl, ethoxyacetyl, benzyloxycarbonyl, methanesulfonyl, toluenesulfonyl, benzoyl, chlorobenzoyl, methoxybenzoyl, nicotinoyl, isonicotinoyl, thenoyl, furoyl, methylcarbamoyl, p-chloro-m-sulfamoylbenzoyl, propionyl, isobutyryl, octanoyl, phenylpropionyl, cyclohexylpropionyl, heptanoyl and dimethoxybenzoyl groups;
$R^4$ represents a hydrogen atom; and
$R^5$ represents a hydrogen atom, halogen atom, nitro group or methyl group at the 3-position;
the dotted line indicates a single or double carbon-carbon bond between the carbon atoms at the 4- and 5-positions of the pyridazinone system;
and pharmaceutically acceptable acid addition salts thereof.

2. A compound as claimed in claim 1 in which
$R^1$ represents a hydrogen atom;
$R^2$ represents a hydrogen atom or methyl group;
A represents a methylene group;
$R^6$ represents a hydrogen atom;
$R^7$ represents $C_1$–$C_6$ alkyl groups; $C_3$ and $C_4$ alkenyl groups; heterocyclic groups selected from the group consisting of tetrahydrofuryl, tetrahydropyranyl, tetrahydrothiofuryl, tetrahydrothiopyranyl, pyrrolidinyl, piperidyl, imidazolidinyl, oxazolidinyl, thiazolidinyl, morpholinyl, thiomorpholinyl and piperazinyl groups; said heterocyclic groups having at least one substituent selected from the group consisting of methyl, ethyl, benzyl, benzhydryl, chlorobenzhydryl and difluorobenzhydryl; or substituted $C_1$–$C_4$ alkyl groups having at least one substituent selected from the group consisting of $C_1$–$C_4$ alkoxy groups, morpholino groups, thiomorpholino groups, piperazinyl groups, phenyl groups, phenyl groups having at least one substituent selected from the group consisting of halogen, $C_1$–$C_4$ alkyl and $C_1$–$C_4$ alkoxy substituents, pyridyl groups and 1-piperazinyl groups having at the 4-position at least one substituent selected from the group consisting of methyl, ethyl, phenyl, methoxycarbonyl, ethoxycarbonyl, benzyl, hydroxyethyl, chlorophenyl, methoxyphenyl, trifluoromethylphenyl, pyridyl, benzhydryl, chlorobenzhydryl, difluorobenzhydryl, formyl, acetyl, valeryl, 3-butenoyl, chlorobutyryl, ethoxyacetyl, benzyloxycarbonyl, methanesufonyl, toluenesulfonyl, benzoyl, chlorobenzoyl, methoxybenzoyl, nicotinoyl, isonicotinoyl, thenoyl, furoyl, methylcarbamoyl, p-chloro-m-sulfamoylbenzoyl, propionyl, isobutyryl, phenylpropionyl, cyclohexylpropionyl and dimethoxybenzoyl groups; and $R^5$ represents a halogen atom or methyl group at the 3-position.

3. A method of treating cardiac disorders in a mammal comprising administering to said mammal an effective amount of a compound which potentiates myocardial contractivity, and wherein said compound is the compound of claim 1.

4. A method of treating cardiac disorders in a mammal comprising administering to said mammal an effective amount of a compound which potentiates myocrdial contractivity, and wherein said compound is the compound of claim 2.

5. The compound of claim 1 designated 6-{3-chloro-4-[N-(2-[4-acetyl-1-piperazinyl]ethyl)carbamoylmethoxy]phenyl}-4,5-dihydro-3(2H)-pyridazinone and pharmaceutically acceptable salts thereof.

6. The compound of claim 1 designated 5-methyl-6-[3-chloro-4-(N-propylcarbamoylmethoxy)phenyl]-4,5-dihydro-3(2H)-pyridazinone and pharmaceutically acceptable salts thereof.

7. The compound of claim 1 designated 5-methyl-6-[3-chloro-4-(N-butylcarbamoylmethoxy)phenyl]-4,5-dihydro-3(2H)-pyridazinone and pharmaceutically acceptable salts thereof.

8. The compound of claim 1 designated 5-methyl-6-[3-chloro-4-(N-isobutylcarbamoylmethoxy)phenyl]-4,5-dihydro-3(2H)-pyridazinone and pharmaceutically acceptable salts thereof.

9. The compound of claim 1 designated 6-[3-(chloro-4-(N-isobutylcarbamoylmethoxy)phenyl]-4,5-dihydro-3(2H)-pyridazinone and pharmaceutically acceptable salts thereof.

10. The compound of claim 1 designated 5-methyl-6-[3-chloro-4-(N-pentylcarbamoylmethoxy)phenyl]-4,5-dihydro-3(2H)-pyridazinone and pharmaceutically acceptable salts thereof.

11. The compound of claim 1 designated 5-methyl-6-[3-chloro-4-(N-hexylcarbamoylmethoxy)phenyl]-4,5-dihydro-3(2H)-pyridazinone and pharmaceutically acceptable salts thereof.

12. The compound of claim 1 designated 6-{3-chloro-4-[N-(2-ethoxyethyl)carbamoylmethoxy]phenyl}-4,5-dihydro-3(2H)-pyridazinone and pharmaceutically acceptable salts thereof.

13. The compound of claim 1 designated 5-methyl-6-[3-chloro-4-(N-phenethylcarbamoylmethoxy)phenyl]-4,5-dihydro-3(2H)-pyridazinone and pharmaceutically acceptable salts thereof.

14. The compound of claim 1 designated 6-{3-chloro-4-[N-(p-methoxyphenethyl)carbamoylmethoxy]phenyl}-3(2H)-pyridazinone and pharmaceutically acceptable salts thereof.

15. The compound of claim 1 designated 5-methyl-6-{3-chloro-4-[N-(3,4-dimethoxyphenethyl)carbamoylmethoxy]phenyl}-4,5-dihydro-3(2H)-pyridazinone and pharmaceutically acceptable salts thereof.

16. The compound of claim 1 designated 6-{3-fluoro-4-[N-(3,4-dimethoxyphenethyl)carbamoylmethoxy]phenyl}-4,5-dihydro-3(2H)-pyridazinone and pharmaceutically acceptable salts thereof.

17. The compound of claim 1 designated 6-{3-methyl-4-[N-(3,4-dimethoxyphenethyl)carbamoylmethoxy]phenyl}-4,5-dihydro-3(2H)-pyridazinone and pharmaceutically acceptable salts thereof.

18. The compound of claim 1 designated 5-methyl-6-{3-chloro-4-[N-(p-chlorophenethyl)carbamoylmethoxy]phenyl}-4,5-dihydro-3(2H)-pyridazinone and pharmaceutically acceptable salts thereof.

19. The compound of claim 1 designated 6-{3-chloro-4-[N-(2-pyrid-2'-ylethyl)carbamoylmethoxy]phenyl}-4,5-dihydro-3(2H)-pyridazinone and pharmaceutically acceptable salts thereof.

20. The compound of claim 1 designated 5-methyl-6-{3-chloro-4-[N-(2-pyrid-2'-ylethyl)carbamoylmethoxy]phenyl}-4,5-dihydro-3(2H)-pyridazinone and pharmaceutically acceptable salts thereof.

21. The compound of claim 1 designated 6-[3-chloro-4-(N-allylcarbamoylmethoxy)phenyl]-4,5-dihydro-3(2H)-pyridazinone and pharmaceutically acceptable salts thereof.

22. The compound of claim 1 designated 6-{3-chloro-4-[N-(1-benzyl-4-piperidyl)carbamoylmethoxy]phenyl}-4,5-dihydro-3(2H)-pyridazinone and pharmaceutically acceptable salts thereof.

23. The compound of claim 1 designated 6-{3-chloro-4-[N-(2-morpholinoethyl)carbamoylmethoxy]phenyl}-4,5-dihydro-3(2H)-pyridazinone and pharmaceutically acceptable salts thereof.

24. The compound of claim 1 designated 6-{3-chloro-4-[N-(2-morpholinoethyl)carbamoylmethoxy]phenyl}-3(2H)-pyridazinone and pharmaceutically acceptable salts thereof.

25. The compound of claim 1 designated 5-methyl-6-{3-chloro-4-[N-(2-morpholinoethyl)carbamoylmethoxy]phenyl}-4,5-dihydro-3(2H)-pyridazinone and pharmaceutically acceptable salts thereof.

26. The compound of claim 1 designated 6-{3-fluoro-4-[N-(2-morpholinoethyl)carbamoylmethoxy]phenyl}-4,5-dihydro-3(2H)-pyridazinone and pharmaceutically acceptable salts thereof.

27. The compound of claim 1 designated 6-{3-methyl-4-[N-(2-morpholinoethyl)carbamoylmethoxy]phenyl}4,5-dihydro-3(2H)-pyridazinone and pharmaceutically acceptable salts thereof.

28. The compound of claim 1 designated 6-{3-chloro-4-[N-(3-morpholinopropyl)carbamoylmethoxy]phenyl}-4,5-dihydro-3(2H)-pyridazinone and pharmaceutically acceptable salts thereof.

29. The compound of claim 1 designated 6-{3-chloro-4-[N-(2-[4-methyl-1-piperazinyl]ethyl)carbamoylmethoxy]phenyl}-4,5-dihydro-3(2H)-pyridazinone and pharmaceutically acceptable salts thereof.

30. The compound of claim 1 designated 6-{3-chloro-4-[N-(2-[4-phenyl-1-piperazinylethyl)carbamoylmethoxy]phenyl}-4,5-dihydro-3(2H)-pyridazinone and pharmaceutically acceptable salts thereof.

31. The compound of claim 1 designated 6-{3-chloro-4-[N-(2-[4-pyrid-2'-yl-1-piperazinyl]ethyl)carbamoylmethoxy]phenyl}-4,5-dihydro-3(2H)-pyridazinone and pharmaceutically acceptable salts thereof.

* * * * *

UNITED STATES PATENT AND TRADEMARK OFFICE
CERTIFICATE OF CORRECTION

PATENT NO. : 4,914,093
DATED : April 3, 1990
INVENTOR(S) : MORISAWA et al It is certified that error appears in the above-identified patent and that said Letters Patent is hereby corrected as shown below:

Column 11, line 22, change "gastric acid" to
   --acetic acid--.

Column 24, line 17, change "fine" to --find--.

Signed and Sealed this

Eighth Day of September, 1992

Attest:

DOUGLAS B. COMER

Attesting Officer

Acting Commissioner of Patents and Trademarks